US006660832B1

(12) United States Patent
Jefferson et al.

(10) Patent No.: US 6,660,832 B1
(45) Date of Patent: Dec. 9, 2003

(54) MACROCYCLIC COMPOUNDS AND PREPARATION METHODS THEREOF

(75) Inventors: Elizabeth Jefferson, La Jolla, CA (US); Eric Edward Swayze, Carlsbad, CA (US)

(73) Assignee: ISIS Pharmaceuticals, Inc., Carlsbad, CA (US)

(*) Notice: Subject to any disclaimer, the term of this patent is extended or adjusted under 35 U.S.C. 154(b) by 0 days.

(21) Appl. No.: 09/378,529

(22) Filed: Aug. 20, 1999

(51) Int. Cl.$^7$ ................................................. C07K 7/50
(52) U.S. Cl. ........................ 530/317; 514/11; 514/19; 514/159
(58) Field of Search ........................... 530/454, 474, 530/450, 317; 514/183, 11, 19

(56) References Cited

U.S. PATENT DOCUMENTS

| | | | |
|---|---|---|---|
| 3,687,808 A | 8/1972 | Merigan et al. | 435/91.3 |
| 5,741,462 A | 4/1998 | Nova et al. | 422/68.1 |
| 5,751,629 A | 5/1998 | Nova et al. | 365/151 |
| 5,770,455 A | 6/1998 | Cargill et al. | 436/518 |
| 5,874,214 A | 2/1999 | Nova et al. | 435/6 |
| 5,925,562 A | 7/1999 | Nova et al. | 435/287.1 |

OTHER PUBLICATIONS

Corriveau Infectious Agents and Disease 2, 44–52, 1993.*
Gavini, Archiv der Pharmazie 333 (10) 341_6, 2000.*
Fudou, Journal of Antibiotics 54 (2) 149–52, 2001.*
Juvvadi Journal of Peptide Research 53 (3) 244–51, 1999.*
Avrahami, Biochemistry 40 (42) 12591–603, 2001.*
Otvos, Protein Science 9 (4) 742–9, 2000.*
Jefferson et al., Beta–Amino Acid Facilitates Macrocyclic Ring Closure in a Combinatorial Library, Tetrahedron Letters, 40, pp. 7757–7760, 1999.*
Boggetto et al., Cyclic Peptides as Selective Substrates and Suicide Substrate Precursors of Trypsin–like proteinases, Bull. Chim. Fr., 36(11), pp. 152–166, 1994.*
Feng et al., SNAr Cyclization to Form Cyclic Peptidomimetics of Beta–turns., J. Am. Chem. Soc., 120(41), pp. 10768–10769, 1998.*
Kiselyov et al., Tetrahedron, 54 pp. 10635–10640, 1998.*
Rama Rao et al., Chem. Rev., 95, pp. 2135–2167, 1995.*
Marsh et al., J. Org. Chem., 62, pp. 6199–6202, 1997.*
Angell, Y.M., et al., "Comparative Studies of the Coupling of N–Methylated, Sterically Hindered Amino Acids During Solid–Phase Peptide Synthesis", Tetrahedron Lett., 1994, 35, 5981–5984.
Balasubramanian, S., et al., "Solid Phase Reductive Alkylation of Secondary Amines", Tetrahedron Lett., 1996, 37, 4819–4822.
Beugelmans, R., et al., "The First Examples of SnAr–based Macrocyclisation: Synthesis of Model Carboxylate–Binding Pockets of Vancomycin", J. Chem. Soc., Chem. Commun., 1994, 439.

Bilodeau, M.T., et al., "Solid–Supported Synthesis of Imidazoles: A Stragegy for Direct Resin–Attachment to the Imidazole Core", J. Org. Chem., 1998, 63, 2800–2801.
Block, L., "Medicated Applications", Remington's Pharmaceutical Sciences, 18th Ed., Gennaro (ed.), Mack Publishing Co., Easton, PA, 1990, Ch. 87, 1596–1614.
Bodanszky, M., et al., "Side Reactions in Peptide Synthesis. 11. Possible Removal of the 9–Fluorenylmethyoxycarbonyl Group by the Amino Components during Coupling", J. Org. Chem., 1979, 44, 1622–1625.
Bomann, et al., "A Mild, Pyridine–Borane–Based Reductive Amination Protocol", J. Org. Chem., 1995, 60, 5995–5996.
Cheung, S.T., et al., "N–Methylamino acids in peptides synthesis. VI. A method for determining the enantiomeric purity of N–methylamino acids and their derivatives by ion–exchange chromatography as their C–terminal lysyl dipeptides", Can. J. Chem., 1977, 55, 911–915.
Chow, C.S., et al., "A Structural Basis for RNA—Ligand Interactions", Chem. Rev., 1997, 97, 1489–1514.
Coste, J., et al., "Oxybenzotriazole Free Peptide Coupling Reagents for N–Methylated Amino Acids", Tetrahedron Lett., 1991, 32, 1967–1970.
Coste, J., et al., "BROP: A New Reagent for Coupling N–Methylated Amino Acids", Tetrahedron Lett., 1990, 31, 669–672.
Egorov, M.P., et al., "Some Aspects of Anionic σ Complexes", Chem. Rev., 1982, 82, 427–459.
Enantioselective Synthesis of Beta–Amino Acids, Juarish, E., John Wiley & Sons, New York, N.Y. 1997.
Englisch, U., "Chemically Modified Oligonucleotides as Probes and Inhibitors", Angew. Chem. Int. Ed. Eng., 1991, 30, 613–629.
Feng, Y., et al., SNAr Cyclizations To Form Cyclic Peptidomimetics of β–Turns, J. Am. Chem. Soc., 1998, 120, 10768–10769.

(List continued on next page.)

Primary Examiner—Christopher S. F. Low
Assistant Examiner—David Lukton
(74) Attorney, Agent, or Firm—Woodcock Washburn LLP

(57) ABSTRACT

The present invention is directed to macrocyclic compounds of the formula (I)

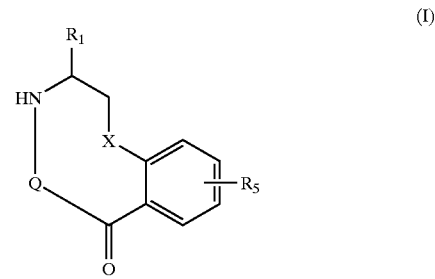

(I)

wherein Q, X, $R_1$ and $R_5$ are as defined herein. Compounds of the invention are useful for therapeutic and prophylactic treatment of bacterial infection in mammals. Solid phase synthetic procedures are provided effecting synthesis of the macrocyclic rings attached to a solid support.

31 Claims, 7 Drawing Sheets

OTHER PUBLICATIONS

Fivush, A.M., et al., "AMEBA: An Acid Sensitive Aldehyde Resin for Solid Phase Synthesis", *Tetrahedron Lett.,* 1997, 38, 7151–7154.

Greene, T.W. and Wuts, P.G.M., Protective Groups in Organic Synthesis, $2^{nd}$ Ed., John Wiley & Sons, New York, N.Y. 1991.

Guichard, G., et al., "Preparation of N–Fmoc–Protected $\beta^2$–and $\beta^3$–Amino Acids and Their Use as Building Blocks for the Solid–Phase Synthesis of β–Peptides", *Helv. Chem. Acta.,* 1998, 81, 187–206.

Hermann, T., "RNA as a drug target: chemical, modelling, and evolutionary tools", *Curr. Opin. Biotech.,* 1998, 9, 66–73.

Kearney, P.C., et al., "Solid–Phase Synthesis of 2–Aminothiazoles", *J. Org. Chem.,* 1998, 63, 196–200.

Kiselyov, et al., "Solid Support Synthesis of 14–Membered Macrocyles Containing the Thioether Bridge via SNAr Methodology", *Tetrahedon,* 1998, 54, 10635–10640.

Kroschwitz, J.I., "Polynucleotides", *Concise Encyclopedia of Polymer Science and Engineering,* 1990, John Wiley & Sons, New York, 858–859.

Longer, M. A. et al., "Sustained–Release Drug Delivery Systems", *Remington's Pharmaceitucal Sciences,* 18th Ed., Gennaro (ed.), Mack Publishing Co., Easton, PA, 1990, Ch. 91, 1676–1693.

Marsh, I.R., et al., "Solid–Phase Total Synthesis of Oscillamide Y and Analogues", *J. Org. Chem.,* 1997, 62, 6199–6203.

McClinton, M.A., "Triethylamine Tris(hydrogen fluoride): Applications in Synthesis", *Aldrichimica Acta,* 1995, 28, 31–35.

Meire, "The Woff Rearrangement of α–Diazo Carbonyl Compounds", *Angew. Chem. Int. Ed. Engl.* 1975, 14, 32–43.

Michael, K., "Designing Novel RNA Binders", *Chem. Eur. J.,* 1998, 4, 2091–2098.

Moormann, A.E., "Reductive Amination of Piperidines with Aldehydes Using Borane–Pyridine", *Synth. Commun.,* 1993, 23, 789–795.

Nairn, et al., "Solutions, Emulsions, Suspensions and Extracts", *Remington's Pharmaceutical Sciences,* 18th Ed., Gennaro (ed.), Mack Publishing Co., Easton, PA, 1990, Ch. 83, 1519–1544.

Nurgatin, et al., "Investigations in the 2,4,6–Trinitrothiophenol Series . . . ", *J. Org. Chem. USSR,* 1983, 19, 343–346.

Ouyang, et al., "Solid Support Synthesis of 2–Substituted Dibenz[b,f]oxazepin–11(10H)–ones via $S_N$Ar Methodology on AMEBA Resin", *Tetrahedron,* 1999, 55, 2827–2834.

Paradisi, C., "Arene Substitution via Nucleophilic Addition to Electron Deficient Arenes", Comprehensive Organic Synthesis, Trost, B.M., et al., eds., Pergamon Press: Oxford, 1991, vol. 4, pp. 423–450.

Pearson, N.D. and Prescott, C.D., "RNA as a drug target", *Chem. Biol.,* 1997, 97(4), 409–414.

Pelter, A., et al., "Reductive Aminations of Ketones and Aldehydes using Borane–Pyridine", *J. Chem. Soc., Perkins Trans I,* 1984, 717–720.

Rama Rao, A.V., et al., "$S_N$Ar Macrycyclisation: A New Approach Towards the Synthesis of D–O–E Segment of vancomycin", *Tetrahedron lett.,* 1997, 38(42), 7433–7436.

Rama Rao, A.V., et al., "Studies Directed toward the Synthesis of Vancomycin and Related Cyclin Peptides", *Chem. Rev.,* 1995, 95, 2135–2167.

Rich, D.H., "Bis(2–oxo–3–oxazolidinyl)phosphinic Chloride (1) as a Coupling Reagent for N–Alkyl Amino Acids", *J. Am. Chem. Soc.,* 1985, 107, 4342–4343.

Rudnic, E. et al., "Oral Solid Dosage Forms", *Remington's Pharmaceutical Sciences,* 18th Ed., Gennaro (ed.), Mack Publishing Co., Easton, PA, 1990, Ch. 89, 1633–1665.

Sarantakis, et al., "Solid Phase Synthesis of Sec–Amides and Removal from the Polymeric Support Under Mild Conditions", *Tetrahedron Lett.,* 1997, 38, 7325–7328.

Swayze, E., "Secondary Amide–based Linkers for Solid Phase Organic Synthesis", *Tetrahedron Letters,* 1997, 38(49), 8465–8468.

Wallis, M.G., et al., "The Binding of Antibiotics to RNA", *Prog. Biophys. Molec. Biol.,* 1997, 67, 141–154.

Wei, G.P., et al., "Solid Phase Synthesis of Benzimidazolones", *Tetrahedron Letts.,* 1998, 39, 179–182.

Wenger, R.M., "270. Synthesis of Cyclosporine", *Helv. Chem. Acta.,* 1983, 66, 2672–2702.

Yoon, N.M., et al., "Selective Reductions. XIX. The Rapid Reaction of Carboxylic Acids with Borane–Tetrahydrofuran. A Remarkably Convenient Procedure for the Selective Conversion of Carboxylic Acids to the Corresponding Alcohols in the Presence of Other Functional Groups", *J. Org. Chem.,* 1973, 38, 2786–2792.

Boggetto, et al., "Cyclic peptides as selective substrates and suicide substrate precursors of trypsin–like proteinases," *Bull. Soc. Chim. Fr.,* 1994, 131, 152–166.

Chemical Abstracts, 119(13), 1993, Columbus, OH, USA), 944; col. 1, the abstract No. 139765x, Wakselman, M., "New mechanism–based inactivators of trypsin–like proteinases," *J. Med. Chem.,* 1993, 36(11), 1539–1547.

Jefferson, E.A., et al., "β–amino acid facilitates macrocyclic ring closure in a combinatorial library," *Tetra. Letts.,* 1999, 40, 7757–7760.

* cited by examiner

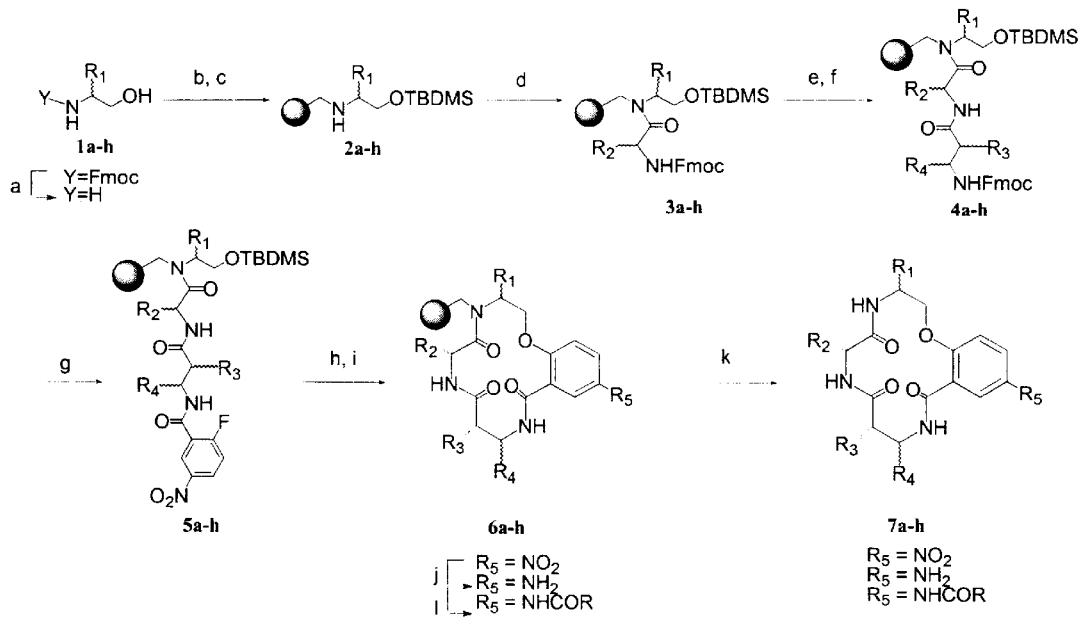

Reagents and Conditions: a) NaOMe, MeOH  b) ArgoGel™-MB-CHO/DIEA/MeOH/trimethylorthoformate, followed by BH$_3$.pyridine/AcOH  c) TBDMS-Cl/DIEA/DMAP/DCM  d) PyBroP/DIEA/DCM/Fmoc-α-amino acid  e) 20% piperidine/DMF  f) Fmoc-ß-amino acid/HATU/collidine/DMF  g) 20% piperidine/ DMF  h) 2-fluoro-5-nitrobenzoic acid/HATU/collidine/DMF/DCM  I) 0.2 M TREAT-HF/THF  j) 0.2 M DBU/DMF  k) 1.5 M SnCl$_2$/DMF/EtOH  l) 95% TFA/5% triisopropylsilane  m) carboxylic acid/HATU/DMF or isocyanate/DMF

Figure 1

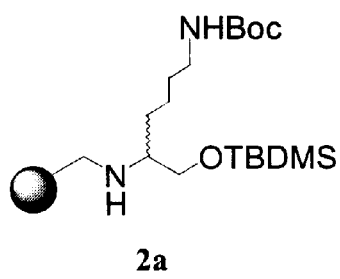 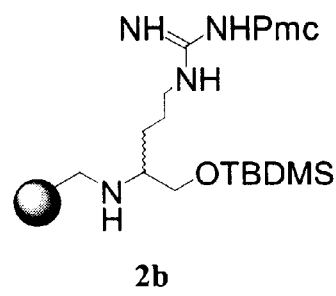 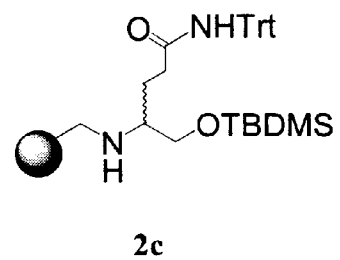 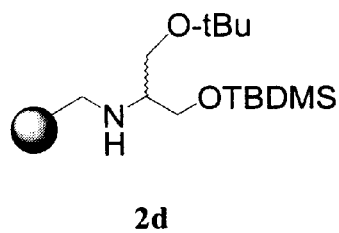 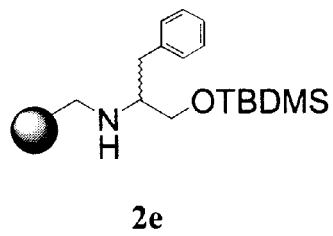 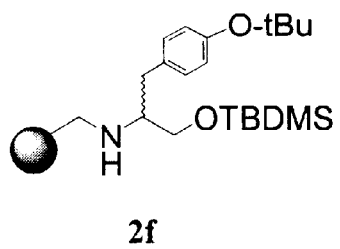 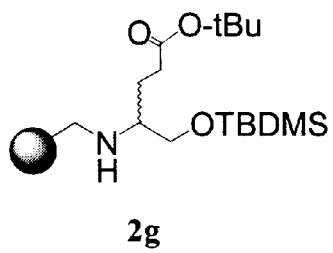 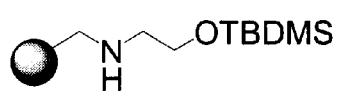
Figure 2

$R_3$ and $R_4$

| H | $NH_2$ | $HO-CH_2$ | $HOOC-CH_2$ | $H_2C-C_6H_4-OH$ |
|---|---|---|---|---|
| 3a | 3b | 3c | 3d | 3e |
| 4a | 4b | 4c | 4d | 4e |

R7 = CH2Ph; MS-EI (+ve): m/z = 853 (M+H)

R7 = H; MS-EI (+ve): m/z = 673 (M+H)

MACROCYCLIC COMPOUNDS AND PREPARATION METHODS THEREOF

FIELD OF THE INVENTION

The present invention is directed to therapeutic compounds, in particular, macrocyclic compounds as well as processes for their synthesis and use thereof in treating bacterial infections.

BACKGROUND OF THE INVENTION

A particular interest in modern drug discovery is the development of novel low molecular weight orally-bioavailable drugs that work by binding to RNA. Recent advances in the determination of RNA structure has lead to new opportunities that will have a significant impact on the pharmaceutical industry. RNA, which serves as a messenger between DNA and proteins, was thought to be an entirely flexible molecule without significant structural complexity. Recent studies have revealed a surprising intricacy in RNA structure. RNA has a structural complexity rivaling proteins rather than simple motifs like DNA. Genome sequencing reveals both the sequences of the proteins and the mRNAs that encode them. Since all proteins are synthesized using an RNA template, all proteins can be inhibited by preventing their production in the first place by interfering with the translation of the mRNA. Since both proteins and the RNAs are potential drug targeting sites, the number of targets revealed from genome sequencing efforts is effectively doubled. These observations unlock a new world of opportunities for the pharmaceutical industry to target RNA with small molecules.

Classical drug discovery has focused on proteins as targets for intervention. Proteins can be extremely difficult to isolate and purify in the appropriate form for use in assays for drug screening. Many proteins require post-translational modifications that occur only in specific cell types under specific conditions. Proteins fold into globular domains with hydrophobic cores and hydrophilic and charged groups on the surface. Multiple subunits frequently form complexes, which may be required for a valid drug screen. Membrane proteins usually need to be embedded in a membrane to retain their proper shape. The smallest practical unit of a protein that can be used in drug screening is a globular domain. The notion of removing a single alpha helix or turn of a beta sheet and using it in a drug screen is not practical, since only the intact protein has the appropriate 3-dimensional shape for drug binding. Preparation of biologically active proteins for screening is a major limitation of classical high throughput screening and obtaining biologically active forms of proteins is an expensive and limiting reagent in high throughput screening efforts.

For screening to discover compounds that bind RNA targets, the classic approaches used for proteins can be superceded with new approaches. All RNAs are essentially equivalent in their solubility, ease of synthesis or use in assays. The physical properties of RNAs are independent of the protein they encode. They may be readily prepared in large quantity through either chemical or enzymatic synthesis and are not extensively modified in vivo. With RNA, the smallest practical unit for drug binding is the functional subdomain. A functional subdomain in RNA is a fragment that, when removed from the larger RNA and studied in isolation, retains its biologically relevant shape and protein or RNA-binding properties. The size and composition RNA functional subdomains make them accessible by enzymatic or chemical synthesis. The structural biology community has developed significant experience in identification of functional RNA subdomains in order to facilitate structural studies by techniques such as NMR spectroscopy. For example, small analogs of the decoding region of 16S rRNA (the A-site) have been identified, containing only the essential region and shown to bind antibiotics in the same fashion as the intact ribosome.

The binding sites on RNA are hydrophilic and relatively open as compared to proteins. The potential for small molecule recognition based on shape is enhanced by the deformability of RNA. The binding of molecules to specific RNA targets can be determined by global conformation and the distribution of charged, aromatic, and hydrogen bonding groups off of a relatively rigid scaffold. Properly placed positive charge may be important, since long-range electrostatic interactions can be used to steer molecules into a binding pocket with the proper orientation. In structures where nucleobases are exposed, stacking interactions with aromatic functional groups may contribute to the binding interaction. The major groove of RNA provides many sites for specific hydrogen bonding with a ligand. These include the aromatic N7 nitrogen atoms of adenosine and guanosine, the O4 and O6 oxygen atoms of uridine and guanosine, and the amines of adenosine and cytidine. The rich structural and sequence diversity of RNA suggests that ligands can be created with high affinity and specificity for their target.

RNA molecules play key roles in essential biological processes, such as protein synthesis, transcriptional regulation, splicing and retroviral replication (Michael, K.; Tor. Y., *Chem. Eur. J.*, 1998, 4, 2091). RNA molecules are promising molecular hosts because of their distinctive architecture of sophisticated secondary and tertiary structures (Pearson, N. D.; Prescott, C. D., *Chem. Biol.*, 1997, 97, 4, 409, Hermann, T.; Westhof, E., *Curr. Opin. Biotech.*, 1998, 9, 66). While our understanding of RNA structure and folding, as well as the modes in which RNA is recognized by other ligands, is far from being comprehensive, significant progress has been made in the last decade (Chow, C. S.; Bogdan, F. M., *Chem. Rev.*, 1997, 97, 1489, Wallis, M. G.; Schroeder, R., *Prog. Biophys. Molec. Biol.* 1997, 67, 141). Despite the central role RNA plays in the replication of bacteria, drugs that target these pivotal) RNA sites of these pathogens are scarce. The increasing problem of bacterial resistance to antibiotics make the search for novel RNA binders of crucial importance.

Bacteria are extremely compelling therapeutic targets for RNA-binding small molecule drugs. The world needs new chemical entities that work against bacteria with broad-spectrum activity by new mechanisms of action. Perhaps the biggest challenge in discovering RNA-binding antibacterial drugs is identifying vital structures common to bacteria that can be disabled by small molecule drug binding. A challenge in targeting RNA with small molecules is to develop a chemical strategy which recognizes specific shapes of RNA. There are three sets of data that provide hints on how to do this: natural protein interactions with RNA, natural product antibiotics that bind RNA, and man-made RNAs (aptamers) that bind small molecules. Each data set provides different insights to the problem. Several classes of drugs obtained from natural sources have been shown to work by binding to RNA or RNA/protein complexes. These include three different structural classes of antibiotics: thiostreptone, the aminoglycoside family and the macrolides family of antibiotics. These examples provide powerful clues to how small molecules and targets might be selected. Nature has selected RNA targets in the ribosome, one of the most ancient and conserved targets in bacteria. Since antibacterial drugs are desired to be potent and have broad-spectrum activity these ancient processes fundamental to all bacterial life represent attractive targets. The closer we get to ancient conserved functions the more likely we are to find broadly conserved RNA shapes. It is important to also consider the shape of the equivalent structure in humans, since bacteria were unlikely to have considered the therapeutic index of their RNAs while evolving them.

A large number of natural antibiotics exist that are directed against ribosomal RNA/protein interactions, RNA structural components, RNA modifying enzymes, DNA modifying enzymes, and transcriptional and translational components. These include the aminoglycosides, kirromycin, neomycin, paromomycin, thiostrepton, and many others. They are very potent, bactericidal compounds that bind RNA of the small ribosomal subunit. The bactericidal action is mediated by binding to the bacterial RNA in a fashion that leads to misreading of the genetic code . Misreading of the code while translating integral membrane proteins is thought to produce abnormal proteins that compromise the barrier properties of the bacterial membrane. This is a very interesting mechanism, since bactericidal action is highly desired in new antimicrobial drugs and there are few ways to achieve it.

Thiostrepton, a cyclic peptide based antibiotic, inhibits several reactions at the ribosomal GTPase center of the 50S ribosomal subunit. Evidence exists that thiostrepton acts by binding to the 23S rRNA component of the 50S subunit at the same site as the large ribosomal protein L11. The binding of L11 to the 23S rRNA causes a large conformation shift in the proteins tertiary structure. The binding of thiostrepton to the rRNA appears to cause an increase in the strength of the L11/23S rRNA interactions and prevents a conformational transition event in the L11 protein thereby stalling translation. Such targeting of the ribosomal "machinery" involved in protein synthesis opens new opportunities for novel therapeutic mechanisms. Unfortunately, thiostrepton has very poor solubility, relatively high toxicity, and is not generally useful as an antibiotic.

The macrolide antibiotics, which include erythromycin, azithromycin, and the streptogramin family among others, work by binding the large ribosomal subunit. The molecular details of the binding site for macrolides are not well understood. Macrolides interfere with the peptidyltransfer function of the ribosome. Whether RNA, protein or the interface of the two provides the binding site for macrolide antibiotics is unclear. However, macrolide structures have very attractive pharmaceutical properties and are good lead shapes for the design of new compound motifs that interact with RNA or RNA/protein complexes.

Antibiotics are chemical substances produced by various species of microorganisms (bacteria, fungi, actinomycetes) that suppress the growth of other microorganisms and may eventually destroy them. However, common usage often extends the term antibiotics to include synthetic antibacterial agents, such as the sulfonamides, and quinolines, that are not products of microbes. The number of antibiotics that have been identified now extends into the hundreds, and many of these have been developed to the stage where they are of value in the therapy of infectious diseases. Antibiotics differ markedly in physical, chemical, and pharmacological properties, antibacterial spectra, and mechanisms of action. In recent years, knowledge of molecular mechanisms of bacterial, fungal, and viral replication has greatly facilitated rational development of compounds that can interfere with the life cycles of these microorganisms.

At least 30% of all hospitalized patients now receive one or more courses of therapy with antibiotics, and millions of potentially fatal infections have been cured. However, at the same time, these pharmaceutical agents have become among the most misused of those available to the practicing physician. One result of widespread use of antimicrobial agents has been the emergence of antibiotic-resistant pathogens, which in turn has created an ever-increasing need for new drugs. Many of these pathogens have also contributed significantly to the rising costs of medical care.

When the antimicrobial activity of a new agent is first tested a pattern of sensitivity and resistance is usually defined. Unfortunately, this spectrum of activity can subsequently change to a remarkable degree, because microorganisms have evolved the array of ingenious alterations discussed above that allow them to survive in the presence of antibiotics. The mechanism of drug resistance varies form microorganism to microorganism and from drug to drug.

The development of resistance to antibiotics usually involves a stable genetic change, heritable from generation to generation. Any of the mechanisms that result in alteration of bacterial genetic composition can operate. While mutation is frequently the cause, resistance to antimicrobial agents may be acquired through transfer of genetic material from one bacterium to another by transduction, transformation or conjugation.

For the foregoing reasons, there remains a need for new chemical entities that possess antimicrobial activity. Further, in order to accelerate the drug discovery process, new synthetic methods are needed to provide an array of compounds that are useful for the treatment microbial infections.

SUMMARY OF THE INVENTION

In an aspect of the invention, there is provided macrocyclic compounds of the formula (I),

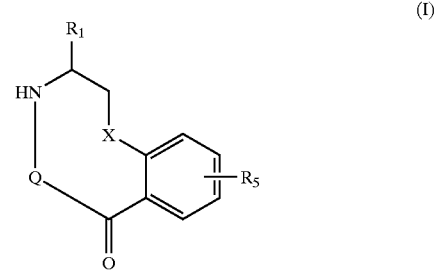

wherein:
  X is O, NH or S;
  Q is a bivalent linker comprising at least two amino acid residues wherein one of said amino acids is a β-amino acid;
  $R_1$ is an amino acid side chain; and
  $R_5$ is H, OH, COOH, halogen, SH, cyano, amino, an electron withdrawing group, alkoxy, —C(O)NH$_2$, —C(O)NHR$_6$, —C(O)-(a.a.)$_{1-4}$, —C(O)OR$_6$, —CH$_2$OH, —CH$_2$OR$_6$, —NHC(O)R$_7$ and —NH-(a.a.)$_{1-4}$ wherein a.a. is an amino acid residue;
  $R_6$ is alkyl optionally substituted with OH, halogen, COOH, cyano, amino, amidine, guanidine, urea, a nucleobase; or $R_6$ is aryl, aralkyl, a heterocycle or a heterocycle-alkyl group optionally substituted with OH, halogen, COOH, oxo, cyano, amino, amidine, guanidine or urea; and
  $R_7$ is alkyl optionally substituted with OH, halogen, COOH, cyano, amino, amidine, guanidine, urea or a nucleobase; or R$_7$ is aryl, aralkyl, a heterocycle or a heterocycle-alkyl group each optionally substituted with OH, halogen, C$_{1-4}$ alkyl, COOH, oxo, cyano, amino, amidine, guanidine or urea.

In another aspect of the invention, there is provided a process for preparing macrocyclic compounds of formula (IIa),

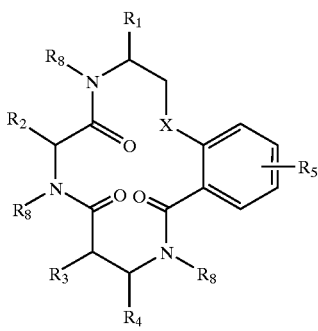

(IIa)

wherein:

X is O, NH or S;

R$_1$ through R$_4$ are each independently H, amino or an amino acid side chain;

R$_5$ is H, OH, COOH, halogen, SH, cyano, amino, an electron withdrawing group, alkoxy, —C(O)NH$_2$, —C(O)NHR$_6$, —C(O)-(a.a.)$_{1-4}$, —C(O)OR$_6$, —CH$_2$OH, —CH$_2$OR$_6$, —NHC(O)R$_7$ and —NH-(a.a.)$_{1-4}$ wherein a.a. is an amino acid residue;

R$_6$ is alkyl optionally substituted with OH, halogen, COOH, cyano, amino, amidine, guanidine, urea, a nucleobase; or R$_6$ is aryl, aralkyl, a heterocycle or a heterocycle-alkyl group optionally substituted with OH, halogen, COOH, oxo, cyano, amino, amidine, guanidine or urea; and R$_7$ is alkyl optionally substituted with OH, halogen, COOH, cyano, amino, amidine, guanidine, urea or a nucleobase; or R$_7$ is aryl, aralkyl, a heterocycle or a heterocycle-alkyl group each optionally substituted with OH, halogen, C$_{1-4}$ alkyl, COOH, oxo, cyano, amino, amidine, guanidine or urea; and R$_8$ is H or a solid support, provided that no more than one R$_8$ is a solid support;

comprising cyclizing a compound of formula (III)

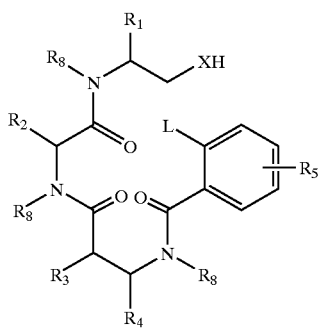

(III)

wherein L is a leaving group; under conditions suitable for aromatic nucleophilic substitution.

In yet another aspect, there is provided methods of treating bacterial infection in a mammal comprising administering to said mammal a therapeutic or prophylactic amount of a macrocyclic compound of the invention.

BRIEF DESCRIPTION OF THE DRAWINGS

FIG. 1 is a schematic representation of the solid phase synthesis of a particular combinatorial library of macrocyclic compounds of the invention.

FIG. 2 is a structural representation of intermediates 2a through 2h from the scheme of FIG. 1.

Figure 3:
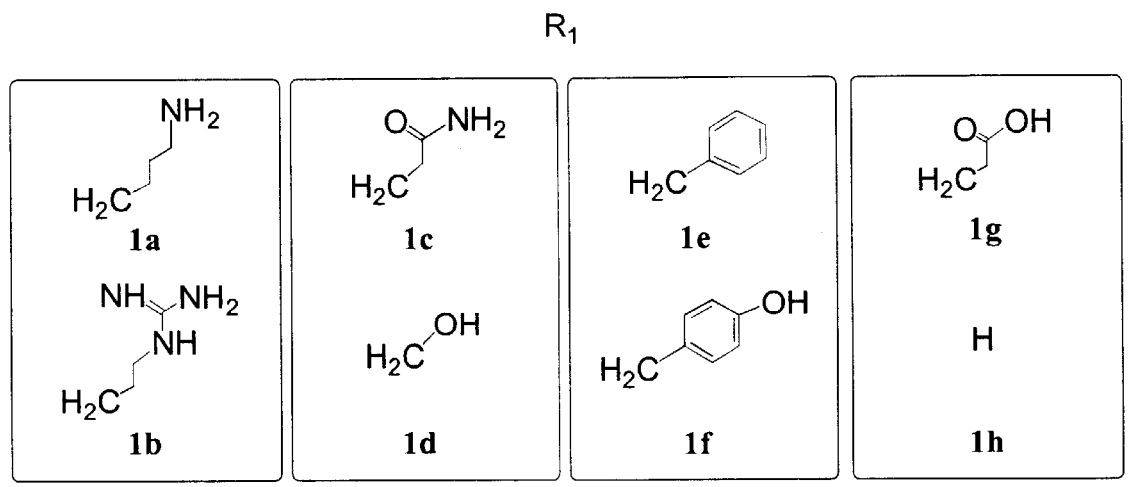
FIG. 3 is a structural representation of R$_1$ substituents from the scheme of FIG. 1.
Figure 4:
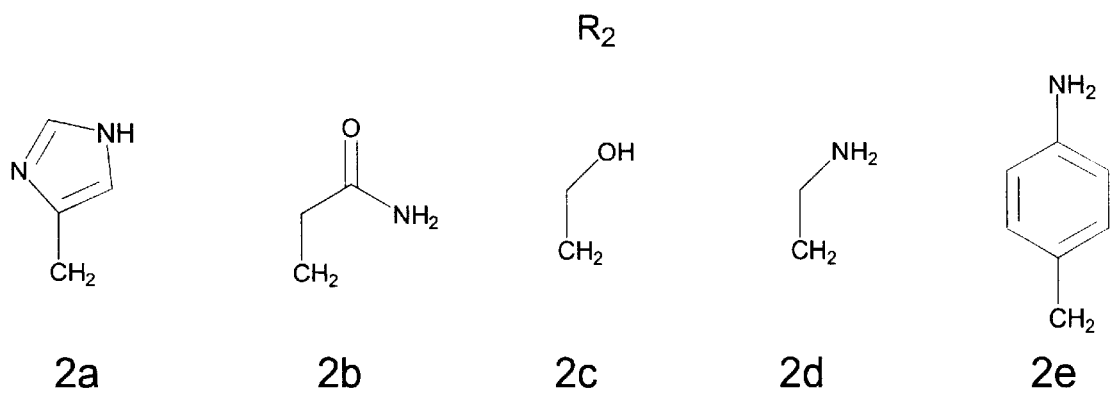
FIG. 4 is a structural representation of R$_2$ substituents from the scheme of FIG. 1.
Figure 5:
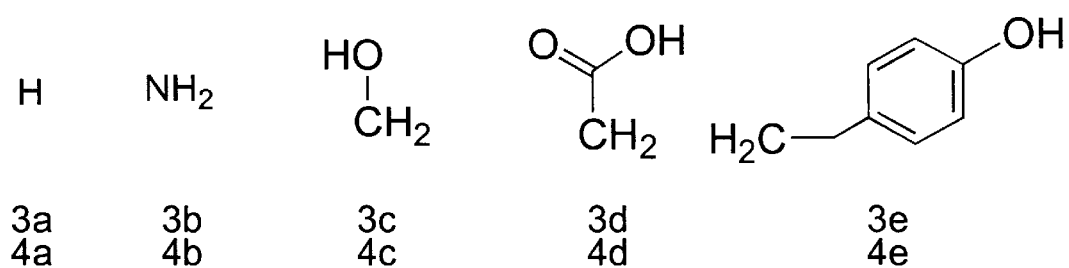
FIG. 5 is a structural representation of substituents R$_3$ and R$_4$ from the scheme of FIG. 1.
Figure 6:
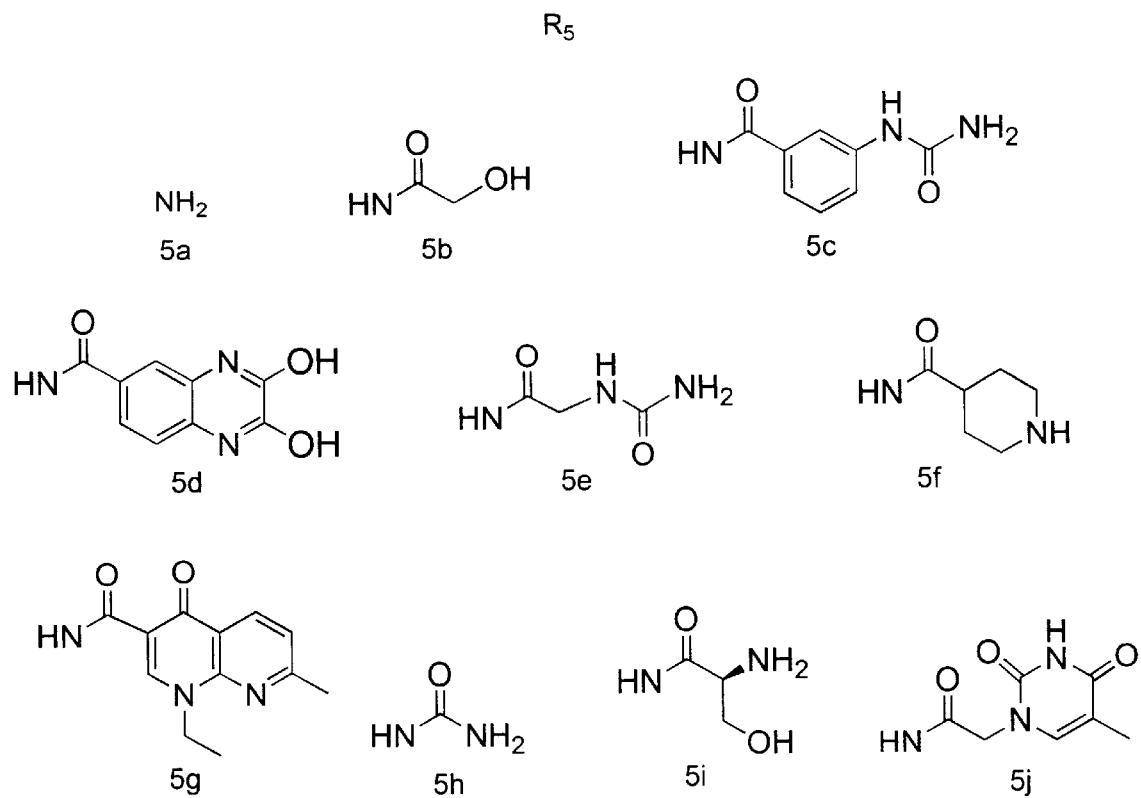
FIG. 6 is a structural representation of R$_5$ substituents from the scheme of FIG. 1.

The present invention is directed to macrocyclic compounds, especially to antibacterial macrocyclic compounds and methods for their synthesis. Compounds of the invention have anti-microbial activity to destroy or inhibit the growth or reproduction of disease-causing microorganisms. In one aspect of the invention there is provided macrocyclic compounds having the general formula (I),

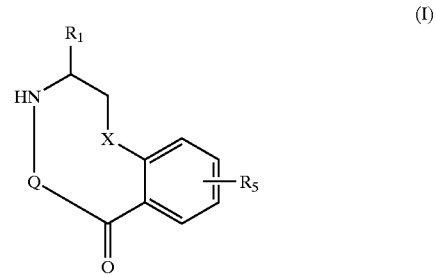

(I)

wherein:

X is O, NH or S;

Q is a bivalent linker comprising at least two amino acid residues wherein one of said amino acids is a β-amino acid;

R$_1$ is an amino acid side chain;

R$_5$ is H, OH, COOH, halogen, SH, cyano, amino, an electron withdrawing group, alkoxy, —C(O)NH$_2$, —C(O)NHR$_6$; —C(O)-(a.a.)$_{1-4}$, —C(O)OR$_6$, —CH$_2$OH, —CH$_2$OR$_6$, —NHC(O)R$_7$ and —NH-(a.a.)$_{1-4}$ wherein a.a. is an amino acid residue;

R$_6$ is alkyl optionally substituted with OH, halogen, COOH, cyano, amino, amidine, guanidine, urea, a nucleobase; or R$_6$ is aryl, aralkyl, a heterocycle or a heterocycle-alkyl group optionally substituted with OH, halogen, COOH, oxo, cyano, amino, amidine, guanidine or urea; and R$_7$ is alkyl optionally substituted with OH, halogen, COOH, cyano, amino, amidine, guanidine, urea or a nucleobase; or R$_7$ is aryl, aralkyl, a heterocycle or a heterocycle-alkyl group each optionally substituted with OH, halogen, C$_{1-4}$ alkyl, COOH, oxo, cyano, amino, amidine, guanidine or urea.

In a preferred embodiment of the invention, X is O.

Q is a dipeptide wherein at least one amino acid of said dipeptide is a β-amino acid. Preferred β-amino acids are selected from the group consisting of β-alanine, β-aspartic acid, 2,3-diaminopropionic acid, β-homoserine and β-homotyrosine. The other amino acid may be an α-amino acid selected from the group consisting of alanine, 4-aminophenylalanine, arginine, asparagine, 2,4-diaminobutyric acid, glutamic acid, glutamine, histidine, isoleucine, leucine, phenylalaninen or serine.

Preferably $R_1$ is the amino acid side chain of alanine, arginine, glutamic acid, glutamine, glycine, lysine, phenylalanine, serine or tyrosine. In a particular embodiment $R_1$ is the side chain of an amino acid that is positively charged at physiological pH.

Preferably $R_5$ is $NO_2$, $NH_2$ or —$NHC(O)R_7$ and is in the position ortho, or more preferably para, to X. Preferably $R_7$ is $NH_2$ or alkyl substituted with $NH_2$, OH, urea, a nucleobase or a nitrogenous heterocycle optionally substituted with $C_{1-4}$ alkyl or oxo (=O). Alternatively $R_7$ is aryl substituted with urea or $R_7$ is a nitrogenous heterocycle optionally substituted with $C_{1-4}$ alkyl or oxo. By "aryl" is meant any aromatic carbocycle or heterocyclic ring or ring system. By "heterocycle" is meant herein to be a mono, bi or tricyclic ring system wherein at least one heteroatom (i.e. N, O or S) is present and may be wholly or partially saturated or unsaturated. A heterocycle substituent may be attached via any position on the ring system as may be synthesized according to established organic synthetic techniques. By "electron-withdrawing groups" are meant chemical functional groups that can give a molecule a dipole moment. A dipole moment is a property of a molecule that results from charge separations. Functional groups can be classified as electron-withdrawing or electron-donating groups relative to hydrogen. Representative electron-withdrawing groups for $R_5$ include but are not limited to diazo, iminium ion, nitroso, nitro, sulfonate ester, trialkyl amine, trifluoromethyl, cyano, carboxyl, sulfate or halogen. A preferred embodiment is the nitro group.

In a preferred embodiment of the invention $R_5$ is $NH_2$ or —$NHC(O)R$. wherein $R_7$ is $NH_2$, pyrazin-2-yl, piperidin-4-yl, —$CH_2$-thymine, 3-urea-phenyl, urea-methyl, hydroxymethyl, 2,3-quinoxalin-7-yl, 1-ethyl-7-methyl-1,8-napthyridin-4-one-3-yl.

$R_6$ is alkyl optionally substituted with OH, halogen, COOH, cyano, amino, amidine, guanidine, urea, a nucleobase; or $R_6$ is aryl, aralkyl, a heterocycle or a heterocycle-alkyl group optionally substituted with OH, halogen, COOH, oxo, cyano, amino, amidine, guanidine or urea. By "alkyl" is meant a saturated or unsaturated (i.e. alkenyl or alkynyl), straight or branched chain of 1 to 12 carbon atoms. Preferred alkyl groups are 1 to 6 carbon atoms and more preferably 1 to 4 i.e. methyl, ethyl, propyl, butyl (n, s, I or t).

Preferred compounds of the invention include but are not limited to:

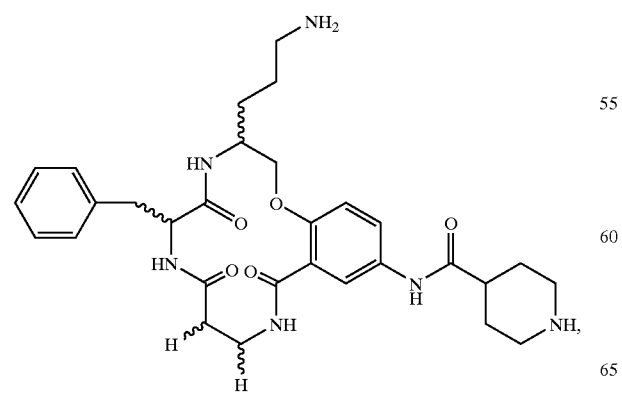

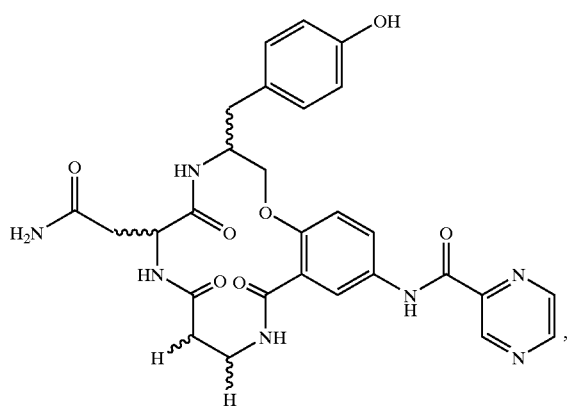

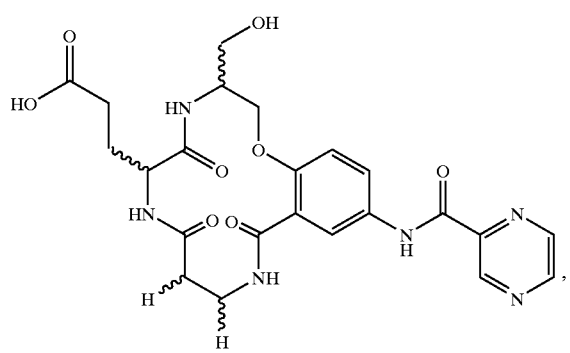

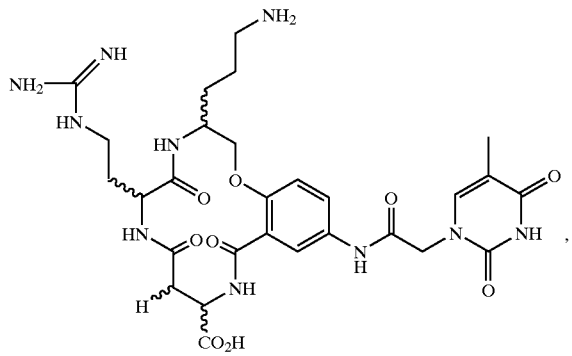

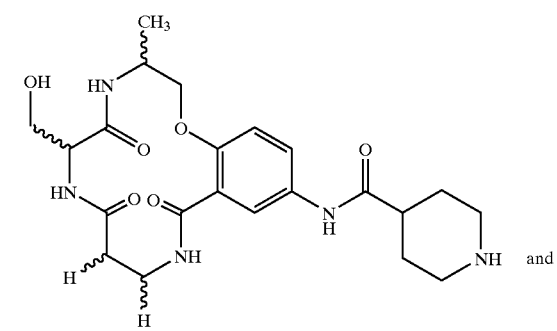

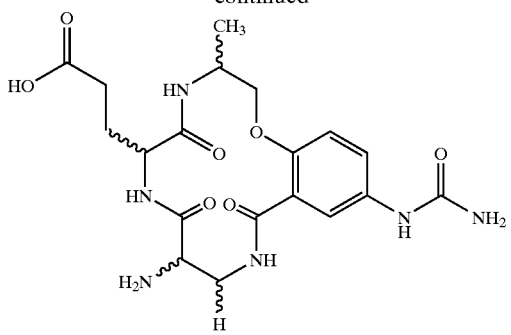

and salts, solvates and hydrates thereof.

It will be appreciated that compounds of the invention may incorporate chiral centers and therefore exist as geometric and stereoisomers. All such isomers are contemplated and are within the scope of the invention whether in pure isomeric form or in mixtures of such isomers as well as racemates.

Amino acids (amino acids) are any of a group of organic molecules that consist of a basic amino group, an acidic carboxyl group, and an organic R group (amino acid side chain) and include naturally occurring, non-naturally occurring, α- and β-amino acids unless otherwise specified.

α-Amino Acids:

Although, more than 100 amino acids occur naturally, only 20 are commonly used in protein synthesis. These are the same in all living organisms, from protozoa to plants and animals. Amino acids can be classified as L or D according to their stereochemistry. All naturally occurring amino acids found in proteins belong to the L stereochemical series. The properties common to all amino acids are due to the relative special arrangements of the carboxyl and amino groups. The physical and chemical properties unique to each amino acid are the result of the structure and chemical properties of the R group. Amino acids are generally grouped according to the polarity (the tendency to interact with water at a neutral pH) and charge of the R group. Naturally occurring amino acids with non-polar R groups include: alanine, valine, leucine, isoleucine, proline, phenylalanine, tryptophane, and methionine. Naturally occurring amino acids with uncharged polar R groups include: glycine, serine, threonine, cysteine, tyrosine, asparagine, and glutamine. Naturally occurring amino acids with acidic R groups include: aspartic acid and glutamic acid. Naturally occurring amino acids with basic R groups include: lysine, arginine, and histidine. Some naturally occurring rare amino acids include: 4-hydroxyproline, 5-hydroxylysine, ε-N-methyllysine, 3-methylhistidine, desmosine, isodesmosine, homocysteine, homoserine, citrulline, ornithine, canavanine, djenkolic acid, and β-cyanoalanine. Non-naturally occurring amino acids are those not found in nature but are capable of being synthesized by procedures known in the art of organic synthesis.

Amino acids can also be classified according to their side chains. The amino acid side chain R group can be an aliphatic, alicyclic, aryl or a heterocyclic group including both non-aromatic heterocycles and aromatic heterocycles (heteroaryl groups) as defined below.

Aliphatic and alicyclic groups suitable for use in the invention include but are not limited to saturated and unsaturated, straight and branched chain and alicyclic, substituted and unsubstituted alkyl, alkenyl and alkynyl groups including ($C_1$–$C_{12}$) methyl, ethyl, propyl, butyl, pentyl, hexyl, heptyl, octyl, nonyl, decyl and other higher carbon straight-chain alkyl groups; isopropyl, isobutyl, sec-butyl, tert-butyl, 1,1,2-trimethylpropyl, 2-methyl-propyl, 2-methyl-4-ethylbutyl, 2,4-diethylpropyl, 3-propyl-butyl, 2,8-dibutyldecyl, 6,6-dimethyloctyl, 6-propyl-6-butyloctyl, 2-methylbutyl, 2-methylpentyl, 3-methylpentyl, 2-ethylhexyl and other branched-chain groups; vinyl, allyl, crotyl, propargyl, 2-pentenyl and other unsaturated groups; and cyclohexane and cyclopentane as well as other alicyclic groups. Preferred compounds are the $C_1$–$C_{12}$ alkyls, $C_2$–$C_{12}$ alkenes and $C_2$–$C_{12}$ alkynes. Most preferred are the $C_1$–$C_4$ alkyls.

Aryl groups suitable for use in the invention include, but are not limited to phenyl, tolyl, benzyl, naphthyl, anthracyl, phenanthryl, and xylyl. These aryl groups may be substituted with any of the above mentioned aliphatic and alicyclic groups.

Heterocyclic groups suitable for use in the invention include both non-aromatic heterocycles and aromatic heterocycles (heteroaryl groups).

Non-aromatic heterocyclic groups suitable for the invention include but are not limited to epoxide, oxetane, tetrahydrofuran, tetrahydropyran, dihydropyran, dioxane, trioxane, ethylenesulfide, thietane, tetrahydrothiophene, tetrahydrothiopyran, dithiane, trithiane, aziridine, azetidine, pyrrolidine, piperidine, homopiperidine, piperazine, homopiperazine, triazine, quinuclidine, decahydroquinoline, oxazole, morpholine, thiazolidine, thiomorpholine, gamma-butyrolactone, delta-valerolactone, thiolactone and others.

Aromatic heterocyclic (heteroaryl) groups suitable for the invention include but are not limited to pyrrole, furan, thiophene, pyrazole, imidazole, triazole, tetrazole, oxazole, oxadiazole, thiazole, thiadiazole, indole, carbazole, benzofuran, benzothiophene, indazoles, benzimidazole, benzotriazole, benzoxazole, benzthiazole, benzothiadiazole, purines, pyridine, pyridazine, pyrimidine, pyrazine, triazine, quinoline, acridine, isoquinoline, cinnoline, phthalazine, quinazoline, quinoxaline, phenazine, phenanthroline, a nucleobase and others.

A nucleobase is any of the purine or pyrimidine bases including but not limited to adenine, guanine, thymine, uracil or cytosine which may be substituted with any of the described aliphatic, alicyclic, aryl or heterocyclic groups or other substituent groups described herein. Nucleobases include synthetic and natural nucleobases such as xanthine, hypoxanthine, 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 8-halo, amino, thiol, thioalkyl, hydroxyl and other 8-substituted adenines and guanines, 5-trifluoromethyl and other 5-substituted uracils and cytosines, 7-methylguanine. Further purines and pyrimidines include those disclosed in U.S. Pat. No. 3,687,808, those disclosed in the *Concise Encyclopedia Of Polymer Science And Engineering*, pages 858–859, Kroschwitz, J. I., ed. John Wiley & Sons, 1990, and those disclosed by Englisch et al., *Angewandte Chemie, International Edition*, 1991, 30, 613, incorporated herein by reference. Certain of these nucleobases are particularly useful for increasing the binding affinity to complementary nucleobases. These include 5-substituted pyrimidines, 6-azapyrimidines and N-2, N-6 and O-6 substituted purines, including 2-aminopropyladenine, 5-propynyluracil and 5-propynylcytosine.

Heterocyclic alkyl groups suitable for the invention include but are not limited to the described non-aromatic heterocycles and the aromatic heterocycles which are each independently attached to any of the above described alkyl groups.

Substituent groups for the above aliphatic, alicyclic, aryl and heterocyclic groups include but are not limited to halogen (fluoro, chloro, bromo, iodo), hydroxyl (OH), thiol (SH), carboxy (COOH), carboxy ester (COOR), amide or carboxamide (CONHR where R is hydrogen, aliphatic, alicyclic, aryl or a heterocyclic group), urea (NHCONHR where R is hydrogen, aliphatic, alicyclic, aryl or a heterocyclic group), aldehyde (CHO), keto (C=O), oxo (=O), nitrile (CN), amidinoamino or guanidino (—NH—C(NH)NH$_2$), trifluoromethyl (CF$_3$), trifluoromethoxy (OCF$_3$), O-alkyl, ether, O-aryl, S-alkyl, thioether, disulfide, S-aryl or amino including NH-alkyl, N-dialkyl, NH-aryl and amine (NH$_2$).

For the twenty common amino acids: alanine (R=alkyl or methyl), valine (R branched alkyl or isopropyl), leucine (R=branched alkyl or isobutyl), isoleucine (R branched alkyl or sec-butyl), proline, phenylalanine (R=aryl or benzyl), tryptophane (R=heteroaryl or 3-methylindole), methionine (R=(thio)ether or (thio)methyl ethyl ether), glycine (R=hydrogen, H), serine (R=(hydroxyl)alkyl or (hydroxyl) methyl), threonine (R=(hydroxyl)alkyl or 1-(hydroxyl)ethyl), cysteine (R=(thiol)alkyl or (thiol)methyl), tyrosine (R=substituted aryl or 4-(hydroxyl)benzyl), asparagine (R=alkyl (carboxamide) or (methyl)carboxamide), glutamine (R=alkyl (carboxamide) or (carboxamide)-2-ethyl), aspartic acid (R=(carboxy)alkyl or (carboxy)methyl), glutamic acid (R=(carboxy)alkyl or (carboxy)-2-ethyl), lysine (R=(amino)alkyl or 4-(amino)butyl), arginine (R=(amadinoamino)alkyl or 3-(amadinoamino)propyl), and histidine (R=heteroaryl or 5-(methyl)imidazole).

Some commercially available (Aldrich) non-aromatic amino acids include but are not limited to the following: glycine, alanine, alpha-aminocyclohexanepropionic acid, 3-chloroalanine, 2-aminoisobutyric acid, 2-aminobutyric acid, valine, tert-leucine, norvaline, 2-amino-4-pentenoic acid, isoleucine, leucine, norleucine, 2,3-diaminopropionic acid, 2-aminocaprylic acid, serine, homoserine, canavanine, threonine, 5-hydroxylysine, 1-amino-1-cyclopropanecarboxylic acid, 1-amino-1-cyclopentanecarboxylic acid, 1-amino-1-cyclohexanecarboxylic acid, 5-amino-1,3-cyclohexadiene-1-carboxylic acid, 2-amino-2-norboranecarboxylic acid, 2,4-diaminobutyric acid, ornithine, lysine, epsilon-methyl-lysine, alpha-2-[(2-aminoethoxy)vinyl]glycine, aspartic acid, glutamic acid, 2-aminoadipic acid, 2,6-diaminopimelic acid, gamma-carboxyglutamic acid, cysteine, pencillamine, homocysteine, S-methylcysteine, methionine, tert-butyl-thiocysteine, ethionine, S-carboxymethylcysteine, lanthionine, cystine, pencillamine disulfide, albizzin, asparagine, lysine, glutamine, citrulline, arginine, epsilon-nitro arginine, homoarginine and S-carbamyl-cysteine.

Some commercially available (Aldrich) aromatic amino acids include but are not limited to the following: 2-phenylglycine, phenylalanine, beta-methylphenylalanine, homophenylalanine, S-benzyl-cysteine, S-trityl-cysteine, 2-fluorophenylglycine, 2-fluorophenylalanine, 3-fluorophenyl-alanine, 4-fluorophenylalanine, 4-chlorophenylalanine, 4-bromophenylalanine, 4-iodophenylalanine, 3,3', 5-triiodo-thyronine, thyroxine, tyrosine, 4-hydroxyphenylglycine, tyrosine, O-methyltyrosine, 3-fluorotyrosine, 3-iodotyrosine, 3-nitrotyrosine, 3,5-diiodotyrosine, 3,4-dihydroxy phenylalanine, 3-(2,4,5-trihydroxyphenyl)alanine, 3-aminotyrosine, 4-aminophenylalanine, 4-nitrohenylalanine, 3,5-dinitrotyrosine, alpha-methyltyrosine, O-benzyltyrosine, 3-(3,4-dihydroxyphenyl)-2-methylalanine, 3-phenylserine, 3,4-dihydroxyphenylserine, valine, N-gamma-glutamyl-1-naphthylamide and 4-aminophenylalanine.

β-Amino Acids

A β-amino acid has an additional carbon atom between the amino acid side chain and the carboxylic acid group.

Virtually any α-amino acid can be converted into a β-amino acid by the Arndt-Eistert reaction (Guichard, G.; Abele, S.; Seebach, D., *Helv. Chem. Acta*, 1998, 81, 187, Meier; Zeller, *Angew. Chem. Int. Ed. Engl.* 1975, 14, 32, Angew. Chem. 87, 52). For a review of methods to synthesize β-amino acids see, *Enantioselective Synthesis of Beta-Amino Acids*, Juarish, E., John Wiley & Sons, New York, N.Y., 1997).

Some β-amino acids used in the invention include but are not limited to: N α-(9-fluorenylmethoxy carbonyl)-β-alanine (H$_2$NCH$_2$CH$_2$COOH), N α-(tert-butoxycarbonyl)-D,L-β-aspartic acid, (9-fluorenylmethoxy carbonyl)-D,L-2,3-diaminopropionic acid, N α-(9-fluorenylmethoxy carbonyl)-D,L-β-serine and N α-(9-fluorenylmethoxy carbonyl) O-tert-butyl-D,L-β-tyrosine.

α-Amino Alcohols

α-Amino alcohols (amino alcohols) are any of a group of organic molecules that consist of a basic amino group, a hydroxyl group, and an organic R group (amino alcohol side chain). Some of the amino alcohols utilized are derived from their Fmoc-D,L-amino alcohols. The eight amino alcohols utilized in the invention include but are not limited to: N α-(9-fluorenylmethoxy-carbonyl) ε-N-tert-butoxycarbonyl-D,L-lysinol, N α-(9-fluorenylmethoxy carbonyl) N ε-(Pmc=2,2,5,7,8-pentamethylchroman-6-sulfonyl)-D,L-arginol, N α-(9-fluorenylmethoxycarbonyl) N γ-trityl-D,L-glutaminol, N α-(9-fluorenylmethoxy carbonyl) O-tert-butyl-D,L-serinol, D,L-phenylalaninol, N α-(9-fluorenyl-methoxycarbonyl) O-tert-butyl-D,L-tyrosinol, N α-(9-fluorenylmethoxy carbonyl) D,L-glutaminol-5-tert-butyl ester. Also utilized is ethanolamine. Some commercially available (Aldrich) non-aromatic amino alcohols include but are not limited to the following: 2-amino-1-propanol, 2-amino-1-butanol, 2-amino-2-methyl-1-propanol, 2-amino-1-pentanol, 2-amino-3-methyl-1-butanol, 2-amino-1-hexanol, isoleucinol, leucinol, tert-leucinol, serinol, l-amino-1-cyclopentanemethanol, 2-amino-3-cyclohexyl-1-propanol, 2-aminocyclohexanol, 1-aminomethyl-1-cyclohexanol, 3-amino-1,2-propanediol, 2-amino-2-ethyl-1,3-propanediol, 2-amino-2-methyl-1,3-propanediol, tris (hydroxymethyl)aminomethane, bis-homotris and 1,3-diamino-2-hydroxypropane. Some commercially available (Aldrich) aromatic amino alcohols include but are not limited to the following: 2-amino-3-phenyl-1-propanol, 2-amino-1-phenylethanol, 2-phenylglycine, S-benzyl-cysteinol, 4-chlorophenylalinol, thiomicamine and 1-amino-2-indanol.

In an alternative aspect, macrocyclic compounds of the invention have the general formula (II),

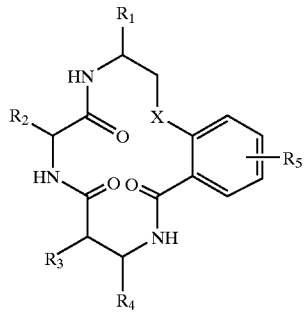

(II)

wherein:

X is O, NH or S;

R₁ through R₄ are each independently H, amino or an amino acid side chain;

R₅ is H, OH, COOH, halogen, SH, cyano, amino, an electron withdrawing group, alkoxy, —C(O)NH₂, —C(O)NHR₆, —C(O)-(a.a.)$_{1-4}$, —C(O)OR₆, —CH₂OH, —CH₂OR₆, —NHC(O)R₇ and —NH-(a.a.)$_{1-4}$ wherein a.a. is an amino acid residue;

R₆ is alkyl optionally substituted with OH, halogen, COOH, cyano, amino, amidine, guanidine, urea, a nucleobase; or R₆ is aryl, aralkyl, a heterocycle or a heterocycle-alkyl group optionally substituted with OH, halogen, COOH, oxo, cyano, amino, amidine, guanidine or urea; and R₇ is alkyl optionally substituted with OH, halogen, COOH, cyano, amino, amidine, guanidine, urea or a nucleobase; or R₇ is aryl, aralkyl, a heterocycle or a heterocycle-alkyl group each optionally substituted with OH, halogen, C$_{1-4}$ alkyl, COOH, oxo, cyano, amino, amidine, guanidine or urea.

A preferred embodiment of the invention is X is O, and R₁ is the amino acid side chain of alanine, arginine, glutamic acid, glutamine, glycine, lysine, phenylalanine, serine or tyrosine.

R₂ is the amino acid side chain of alanine, 4-aminophenylalanine, arginine, asparagine, 2,4-diaminobutyric acid, glutamic acid, glutamine, histidine, isoleucine, leucine, phenylalanine or serine.

R₃ is H, NH₂.

R₄ is H, NH₂ or an amino acid side chain of β-aspartic acid, β-serine or β-tyrosine.

R₅ is NO₂, NH₂ or —NHC(O)R₇ in the position para to X wherein R₇ is NH₂ or alkyl substituted with NH₂, OH, urea, a nucleobase or a nitrogenous heterocycle optionally substituted with C$_{1-4}$ alkyl or oxo or R₇ is aryl substituted with urea or R₇ is a nitrogenous heterocycle optionally substituted with C$_{1-4}$ alkyl or oxo.

In a preferred embodiment of the invention R₅ is NH₂ or —NHC(O)R₇ wherein R₇ is NH₂, pyrazin-2-yl, piperidin-4-yl, —CH₂-thymine, 3-urea-phenyl, urea-methyl, hydroxymethyl, 2,3-quinoxalin-7-yl, 1-ethyl-7-methyl-1,8-napthyridin-4-one-3-yl.

In a preferred embodiment X is O and R₁ and R₂ are independently H, NH₂, COOH or alkyl optionally substituted with OH, SH, alkylthio, NH₂, COOH, amide, guanidine, aryl, OH-substituted aryl, a nitrogenous heterocycle;

R₃ is H, NH₂;

R₄ is H, COOH, hydroxyalkyl or 4-hydroxyphenyl;

R₅ is NO₂, NH₂ or —NHC(O)R₇ in the position para to X wherein R₇ is NH₂ or alkyl substituted with NH₂, OH, urea, a nucleobase or a nitrogenous heterocycle optionally substituted with C$_{1-4}$ alkyl or oxo or R₇ is aryl substituted with urea or R₇ is a nitrogenous heterocycle optionally substituted with C$_{1-4}$ alkyl or oxo.

In a preferred embodiment of the invention R₅ is NH₂ or —NHC(O)R₇ wherein R₇ is NH₂, pyrazin-2-yl, piperidin-4-yl, —CH₂-thymine, 3-urea-phenyl, urea-methyl, hydroxymethyl, 2,3-quinoxalin-7-yl, 1-ethyl-7-methyl-1,8-napthyridin-4-one-3-yl.

In another alternative aspect of the invention, there is provided macrocyclic compounds of general formula (II),

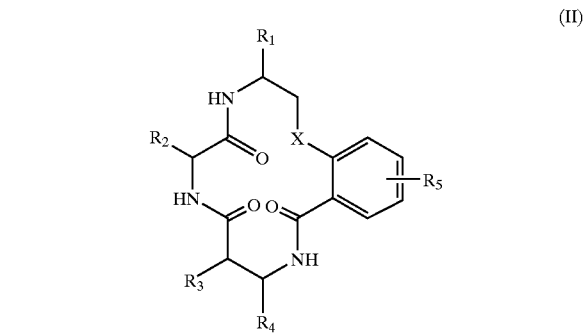

(II)

wherein:

X is O, NH or S;

R₁ through R₄ are each independently H, OH, amino, carboxyl, halogen, cycloalkyl, aryl, a heterocycle, a nucleobase or alkyl optionally substituted with OH, COOH, halogen, oxo, SH, alkylthio, amino, amide, guanidine, amidine, cycloalkyl, aryl, a heterocycle or a nucleobase wherein said cycloalkyl, aryl and heteroaryl groups are optionally substituted with OH, amino, oxo, COOH or halogen;

R₅ is H, OH, COOH, halogen, SH, cyano, amino, an electron withdrawing group, alkoxy, —C(O)NH₂, —C(O)NHR₆, —C(O)-(a.a.)$_{1-4}$, —C(O) OR₆, —CH₂OH, —CH₂OR₆, —NHC(O)R₇ and —NH-(a.a.)$_{1-4}$ wherein a.a. is an amino acid residue;

R₆ is alkyl optionally substituted with OH, halogen, COOH, cyano, amino, amidine, guanidine, urea, a nucleobase; or R₆ is aryl, aralkyl, a heterocycle or a heterocycle-alkyl group optionally substituted with OH, halogen, COOH, oxo, cyano, amino, amidine, guanidine or urea; and R₇ is alkyl optionally substituted with OH, halogen, COOH, cyano, amino, amidine, guanidine, urea or a nucleobase; or R₇ is aryl, aralkyl, a heterocycle or a heterocycle-alkyl group each optionally substituted with OH, halogen, C$_{1-4}$ alkyl, COOH, oxo, cyano, amino, amidine, guanidine or urea.

In another aspect of the invention, there is provided a process for preparing macrocyclic compounds of the general formula (IIa),

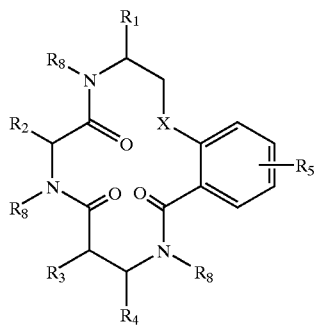

(IIa)

wherein:

X, $R_1$ through $R_5$ are as previously defined and $R_8$ is H or a solid support, provided that no more than one $R_8$ is a solid support; comprising cyclizing a compound of formula (III)

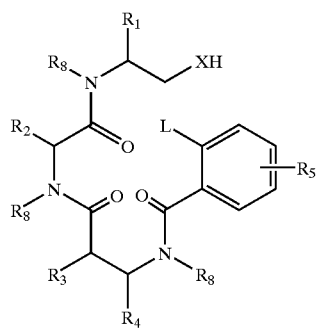

(III)

wherein L is a leaving group;
under conditions suitable for aromatic nucleophilic substitution.

Leaving groups are chemical functional groups that can be displaced from carbon atoms by nucleophilic substitution. Suitable leaving groups include but are not limited to halogen (fluoro (fluorine), chloro, bromo, iodo), alkylsulfonyl, substituted alkylsulfonyl, arylsulfonyl, substituted aryl sulfonyl, heterocyclcosulfonyl or trichloroacetimidate groups. Preferred leaving groups include fluoro, chloro, bromo, iodo, p-(2,4-dinitroanilino)benzenesulfonyl, benzenesulfonyl, methylsulfonyl (mesylate), p-methylbenzenesulfonyl (tosylate), p-bromobenzenesulfonyl, trifluoromethylsulfonyl (triflate), trichloroacetimidate, acyloxy, 2,2,2-trifluoroethanesulfonyl, imidazolesulfonyl, and 2,4,6-trichlorophenyl groups. An especially preferred leaving group is the fluoro group.

The synthesis of macrocyclic compound and libraries thereof, may be accomplished by using solid phase synthesis. While the synthesis is done on solid phase to generate a library of compounds it is known to those skilled in the art that the combinatorial methods may be accomplished employing solution phase synthetic techniques.

The macrocyclic scaffold is particularly attractive as it can be assembled with a diverse array of building block α-amino alcohols (amino alcohols), α-amino acids (amino acids) and β-amino acids. In a particular embodiment, to effect macrocyclization, the nucleophillic aromatic substitution linker, 2-fluoro-5-nitrobenzoic acid is utilized to react with the hydroxyl group of various amino alcohol moieties. The aryl nitro group is an important latent combinatorial diversity site as it can be reduced to the amine and subsequently functionalized with a collection of carboxylic acids. The high purity of the macrocycles synthesized is another salient feature of this library as no purification is required prior to biological testing.

To demonstrate an embodiment of the invention, the synthesis of a library of (15×10×9×10=13,500) compounds on a solid phase support is described as shown in FIG. 1. For a combinatorial library of 13,500 compounds, eight amino alcohols 1a–h are first attached to a solid support resin. The amino alcohols utilized are either commercially available as their Fmoc protected amines or from their free amines (Aldrich, Novabiochem or Bachem). Fmoc is an amino protecting group known as N α-(9-fluorenylmethoxy carbonyl (for other examples of amino protecting groups, see: *Protective Groups in Organic Synthesis*, 2$^{nd}$ ed. T. W. Greene and P. G. M. Wuts, John Wiley & Sons, New York, N.Y., 1991). The amino alcohols can also be derived from their parent α-amino acids (amino acids), for example, by a reduction using the borane-tetrahydrofuran complex (Yoon, N. M.; Pak, C. S.; Brown, H. C.; Krishnamurthy, S.; Stocky, T. P., *J. Org. Chem.*, 1973, 38, 2786). The synthesis of the library is accomplished as a mixture of the D and the L forms of the amino alcohols at $R_1$. The synthesis may be accomplished with either the L or the D amino alcohols at $R_1$. Some of the amino alcohols utilized are derived from their Fmoc-D,L-amino alcohols. The eight amino alcohols utilized include but are not limited to the following: N α-(9-fluorenylmethoxy-carbonyl) ε-N-tert-butoxycarbonyl-D,L-lysinol, N α-(9-fluorenylmethoxy carbonyl) N ε-(Pmc=2,2,5,7,8-pentamethylchroman-6-sulfonyl)-D,L-arginol, N α-(9-fluorenylmethoxy carbonyl) N γ-trityl-D,L-glutaminol, N α-(9-fluorenylmethoxy carbonyl) O-tert-butyl-D,L-serinol, D,L-phenylalaninol, N α-(9-fluorenyl-methoxycarbonyl) O-tert-butyl-D,L-tyrosinol, N α-(9-fluorenylmethoxy carbonyl) D,L-glutaminol-5-tert-butyl ester. Also utilized is ethanolamine. It will be appreciated that except for ethanolamine ($R_1$=H), the D and L isomers (or mixtures) of the Fmoc-amino alcohols may be used to impart specific stereochemistry at $R_1$ in the synthesis.

Other amino alcohols may be utilized for different embodiments of the invention. These include but are not limited to those derived from the naturally occurring amino acids and non-naturally occurring amino acids as previously described.

The amino alcohols 1a–h (FIG. 1) are attached to a resin as described in Examples 1a and 1b. The Fmoc protecting groups are each removed separately by treating each of the Fmoc-amino alcohols with a base. Such bases include but are not limited to piperidine or sodium methoxide. In Example 1a and 1b, the Fmoc groups are separately removed by exposing the amino alcohols 1a–g to sodium methoxide in methanol for several hours followed by neutralization with acetic acid.

The free amino alcohols 1a–h (FIG. 1) are separately attached to a suitable resin by a reductive amination sequence. Suitable resins include but are not limited to derivatized polystyrene resins such as ArgoGel™-MB-CHO resin (eg. 1% cross-linked, particle size 120–130 micron, typical aldehyde loading 0.35–0.45 mmol/g), ArgoGel™-OH and MALDRE™ (Sarantakis et al, Tetrahedron Letters, 1997, 38:42). ArgoGel™-MB-CHO is commercially available from Argonaut Technologies, 887 Industrial Road, Suite G, San Carlos, Calif. 94070 or from Aldrich. The 2-methoxy-4-alkoxy benzaldehyde linker on the ArgoGel resin is attached at the terminus of a polyethylene glycol (PEG) graft portion of the resin via a non-benzylic ether bond. ArgoGel™-MB-CHO is known to be useful for attachment of amines by a reductive amination sequence (Bilodeau, M. T.; Cunningham, A. M., *J. Org. Chem.*, 1998, 63, 2800, Kearney, P. C.; Fernandez, M.; Flygare, J. A., *J. Org. Chem.*, 1998, 63, 196, Swayze, E., *Tetrahedron Lett.*, 1997, 38, (49), 8465). For examples of reductive amination on related aldehyde linkers, see: Fivush, A. M.; Willson, T. M. *Tetrahedron Lett.* 1997, 38, 7151, Sarantakis, D.; Bicksler, J. J. *Tetrahedron Lett.* 1997, 38, 7325.

The borane-pyridine complex (BAP) is used in the reductive amination of aldehydes and ketones because it offers handling convenience due to its relative air stability (Moormann, A. E., *Synth. Commun.*, 1993, 23, 789, Pelter, A.; Rosser, R. M., *J. Chem. Soc., Perkins Trans.* 1, 1984, 717). BAP is also used as the hydride source in the solid phase reductive alkylation of primary and secondary amines to overcome the inherent instability of the iminium ion intermediate (Balasubramanian, S.; Arumugam, V.; Khan, N. M., *Tetrahedron Lett.* 1996, 37, 4819, Bomann, M. D.; Guch, I. C.; DiMare, M., *J. Org. Chem.*, 1995, 60, 5995).

The BAP reagent is a useful way to attach small organic molecules to ArgoGel™-CHO resin. Primary and secondary amines are known in the art to react with aldehydes to give iminium ions. Under BAP hydride reduction conditions, the initially formed iminium ion is reduced to give the amine attached to the resin. A procedure for separately loading each of the eight amino alcohols described above onto ArgoGel™-MB-CHO resin is provided in Example 1a for 1a–d, f, g (FIG. 1) and in Example 1b for 1e and 1h (FIG. 1).

The primary alcohols of the eight amino-alcohol derivatized resins are subsequently protected after an appropriate work-up including a filtration, washing and drying of the resin. A suitable protecting group for the primary alcohol includes but is not limited to silyl ethers such as the tert-butyldimethylsilyl (TBDMS) ether. Addition of tert-butyl dimethyl silyl chloride (TBDMS-Cl), triethylamine and 4-dimethylaminopyridine (DMAP) to the eight amino derivatized resins suspended in dichloromethane is also described in Example 1a for 2a–d, f, g (FIGS. 1 and 2) and in Example 1b for 2e and 2h (FIGS. 1 and 2). Other useful protecting groups that are suitable for the protection of the hydroxyl functionality are given in *Protective Groups in Organic Synthesis*, $2^{nd}$ ed,. Greene, T. W.; Wuts, P. G. M., John Wiley & Sons, New York, N.Y., 1991.

The eight (TBDMS) protected amino derivatized resins are constructed into a library of 4×10×5×10=2,000 members using the "directed sorting" technology as developed by IRORI and described in the following issued U.S. Pat. Nos.: 5,925,562; 5,874,214; 5,751,629; 5,741,462 and 5,770,455 which are incorporated here by reference (IRORI, 11149 North Torrey Pines Road, La Jolla, Calif. 92037).

IRORI's AccuTag-100 combinatorial chemistry system produces large numbers of discrete compounds by using the "directed sorting" split-and-pool technique and Rf labeled microreactors. This technique combines the advantages of the split-and-pool synthesis and parallel synthesis methods for solid phase synthesis.

An advantage of parallel synthesis is that it can yield discrete compounds in multi-milligram quantities. The drawback is the limited number of compounds that can be synthesized per unit time and per reaction. The split-and-pool technique, conversely, addresses these limitations, but imposes others. Compounds produced using this process are no longer discrete, but rather are present as mixtures which must be deconvoluted using various tagging and screening techniques. IRORI's technology of directed sorting takes advantage of the productivity gains of the split-and-pool technique to generate large compound libraries yet can afford discrete compounds (no mixtures) synthesized in multi-milligram quantities. Library generation can be accomplished by using either manual or automated operations. Typical library sizes of discrete compounds made by the directed sorting technique in the manual mode are typically in the range of several hundred to a thousand compounds.

Microreactors are miniaturized devices which contain both a functionalized solid phase support and a unique tag identifier. Miniature radiofrequency (Rf) tags are used as a non-invasive way of labeling compounds. By splitting and pooling microreactors using a process known as "directed sorting" one discrete compound can be synthesized in each microreactor and only one copy of each compound is synthesized.

There are currently two types of microreactors available from IRORI, the Kan™ and Tube™ reactors. There are 3 sizes of Kan™ reactors available which may be used interchangeably. The three sizes of Kan™ reactors are the MicroKan™, the MiniKan™ and the MacroKan™. Typically about 30–300 mg of most commercial resins are loaded into a Kan™ leaving enough space available for the resin to swell and still remain loose within the Kan™. The appropriate Kan™ size can be selected from the list below.

MicroKan™

Up to 30 mg resin capacity

330 μL internal volume

Up to 36 mmol functional loading, (0.2–1.2 mmol/mg)

Up to 10.8 mg compound generated, (Nominal compd. wt.)

MiniKan™

Up to 60 mg resin capacity

660 μL internal volume

Up to 72 mmol functional loading, (0.2–1.2 mmol/mg)

Up to 21.6 mg compound generated, (Nominal compd. wt.)

MacroKan™

Up to 300 mg resin capacity 2.4 mL internal volume

Up to 360 mmol functional loading, (0.2–1.2 mmol/mg)

Up to 108 mg compound generated, (Nominal compd. wt.)

Kan™ reactors are rigid containers made of high grade polypropylene with a polypropylene mesh side walls and are designed to be loaded with solid phase resin beads and an Rf tag. A single compound can be synthesized in each container. The Kan™ is filled with the solid phase resin and the Rf tag before being used in the synthesis. The synthesis takes place by the flow of reagents through the outer mesh walls of the Kan™. Syntheses are performed using normal laboratory glassware and apparatus for heating, cooling, and mixing. Virtually any synthetic chemistry which can be performed using loose solid phase resin and conventional laboratory glassware can be done in the Kans™ reactors. Below is a list of recommended solvents and temperatures for use with the Kans™.

| Solvent | Max Temp. (° C.) |
| --- | --- |
| Toluene* | 70 |
| Benzene* | 70 |
| Hexanes* | 50 |
| Methanol (MeOH) | 64 |
| Ethanol (EtOH) | 78 |
| Tetrahydrofuran (THF) | 65 |
| N,N-Dimethylformamide (DMF) | 85 |
| N,N-Dimethylacetamide (DMA) | 50 |
| N-Methylpyrrolidinone (NMP) | 50 |
| 1,2-Dichloroethane (DCE) | 60 |
| Pyridine (Pyr) | 80 |
| Dichloromethane (DCM) | 40 |

*Recommended use at room temperature

A miniature Rf tag which has a unique label laser etched on its chip, is used to identify and track the compound during the sorting process which occurs between chemical synthesis steps. The glass-encased Rf tag is read by a radio frequency scanner to give a unique identification for each microreactor or MicroKans™ and therefore each compound. Use of the Rf tags provides a convenient and positive identification of compounds for archival and storage purposes at the conclusion of the synthesis procedure.

In each reaction step in the "directed sorting" approach to solid phase combinatorial chemistry, all MicroKans™ which share a common building block reagent are pooled together into a single reaction flask. For a library with 2,000 members, 2,000 MicroKans™ are used and each one is assigned to a specific compound in the first directed sorting step. In subsequent sorting steps, the tag ID is read, the compound is looked up in the database and it is sorted into the proper reactor location.

Synthesis Manager™ is the software that controls and runs the "directed sorting" approach to library synthesis. It records and assigns a code to each Rf tag in each MicroKans™ in the first step and then in subsequent steps directs the sorting of the MicroKans™ to ensure that the proper synthesis of all the compounds is carried out.

Typical library sizes of discrete compounds made by the directed sorting technique in the manual mode are typically in the range of several hundred to a thousand compounds. An LED Sorting Indicator increases the speed of manual sorting and assures the accuracy of the sorting. The LED Sorting Indicator includes 48 labeled LED clips. Each LED clip may be attached to a flask or container into which the MicroKans™ are being sorted. As each MicroKans™ is sorted using the Synthesis Manager software, the appropriate LED is illuminated to make the job easier, faster, and more reliable.

The directed sorting technique may also be automated (AutoSort-10K) for use with libraries in the range of 1,000 to 10,000 compounds. By automating the reaction and cleavage sorting operations, large libraries of discrete compounds can be generated rapidly and efficiently. A microreactor hopper stores up to ten thousand MicroKans™ and automatically feeds them into the vibratory feeder bowl. The MicroKans™ are automatically dispensed from the vibratory feeder bowl and passed through the integrated radio frequency (Rf) scanner. Its database record is then retrieved from Synthesis Manager software, and automatically sorted to the appropriate location.

Converting an existing "loose-resin" synthetic chemistry procedure to a procedure optimized for the MicroKan™ reactor is usually a straightforward process. It is desirable to begin with a well characterized synthesis procedure that has been demonstrated to provide the desired results using loose resin. Adapting a well characterized method to MicroKan™ reactors is usually a matter of adjusting mixing times and rates, and optimizing the washing and cleavage steps using the guidelines described below.

A reaction volume of 0.75–1.0 mL per MicroKan™ and reagent concentrations of 0.1–0.5 M are recommended. An extended reaction time to about 1.5–2 times that of a conventional reactions using loose resin are also recommended.

An air bubble is usually entrapped in a MicroKan™ when a solvent is added. The air bubble has to be removed for effective reaction and washing. Two methods are recommended. After all the solvents and reagents have been added, the MicroKans™ are shaken (or stirred) vigorously for a brief period of time (30–60 seconds) to break the air bubbles trapped inside. After the air bubbles are out, the reaction can be proceeded normally. Alternatively, the air bubbles can be removed by applying a moderate vacuum (10–20 mm Hg) to the reaction vessel containing the MicroKans™ and solvents for a brief period of time (5–10 seconds). The air bubbles disappear and the reaction can be proceeded normally.

All the agitating methods for conventional solid phase synthesis except argon bubbling, can be applied to agitate reactions in the MicroKans™. Stirring by conventional means (magnetic or mechanical) can be applied to agitate the MicroKans™ in a round bottom flask. Due to the protection from the rigid MicroKan™ structure, a relatively stronger stirring action can be applied to MicroKan™ reactions than conventional solid phase reactions. A stirring setting of 200–300 rpm is recommended. MicroKan™ reactions can be effectively agitated by shaking on a conventional orbital platform shaker. A setting of 100–300 rpm is recommended. MicroKan™ reactions can also be most effectively agitated by rotating on a vertical rotator/rocker. A slow setting of 10–20 rpm is recommended.

Recommended agitation for ArgoGel™-MB-CHO resin calls for gentle magnetic stirring, swirling or overhead stirring for large resin quantities (>5 g).

The MicroKan™ reactors can be pooled together for washing after the reactions are quenched separately. At least four washing cycles are recommended. Each cycle consists of one washing with methanol (or other solvents which can shrink the resin) and one washing with dichloromethane (or other solvents which can swell the resin) alternately. Each washing is done as the following. After the solvent is added, the air bubbles are removed. The MicroKans™ are agitated for 5–10 min. The bulk of the solvent is then drained. The residual solvent is spun off by briefly centrifuging the MicroKans™ in a filter, or in a glass tube with the lower part filled with 3–5 mm size glass beads or other loose inert supporting materials. The MicroKans™ are then subjected to the next solvent washing.

The physical characteristics of the MicroKan™ reactor are important to consider when selecting the appropriate resin size. The porous MicroKan™ side walls have nominal openings of 74 mm. It is important to load the MicroKan™ reactors with resin which is no smaller than this opening size. Most commercial resins are sold as 100–200 mesh (75–150mm) or 200–400 mesh (38–75mm). The 200–400 mesh (75–38 micron) resins should never be used with MicroKan™ reactors. Using resin in the 25–100 mesh (710–150 micron) range essentially eliminates resin loss. The 100–200 mesh (150–75 micron) resin will provide good results with a minimal loss of resin and this size is readily available for most commercial resins. Sieving resins to an appropriate size is an alternative that can be very effective.

ArgoGel™-MB-CHO resin has a capacity of 0.35–0.45 mmol/g (determined by nitrogen analysis of the 2,4-dinitrophenyl hydrazone derivative) and a bead size of 120–230 micron (95% within). ArgoGel™-MB-CHO can tolerate mildly acidic and basic reaction conditions.

Proper loading of MicroKan™ reactors with solid phase resin is a prerequisite for a successful synthesis. The internal volume of a single MicroKan™ is approximately 0.33 mL. With an RF tag loaded into the MicroKan™, the remaining volume for solid phase resin is approximately 0.20 mL. For most solid phase resins, this volume is sufficient for approximately 30–35 mg of resin. Different resins have different swelling properties and different solvents have varying abilities to swell resins. Depending on the resin type and solvents to be used, one may be able to load slightly more, or need to load slightly less resin. In most cases, one will want to load as much resin as possible and still leave room for the resin to move freely inside the MicroKan™ when the resin is swelled.

To determine the optimal quantity of resin to use, take four MicroKan™ reactors and load 20 mg of resin into the first, 30 mg into the second, 40 mg into the third, and 50 mg into the fourth. Process each of the four MicroKan™ reactors through each of the solvents and heating conditions to be used during your synthesis, and then visually inspect each one. Alternatively, you can expose each MicroKan™ to only the solvent which causes most swelling, if that information is known.

For a synthetic procedure, a resin quantity is selected which does not over-swell the MicroKan™. For example, if the MicroKan™ with 40 mg of resin when completely swelled left no void volume in the MicroKan™, and the MicroKan™ with 30 mg of resin did have a remaining void volume, use the 30 mg of resin for the synthesis.

Dry loading and wet loading are two methods that can be used to load the MicroKans™ with solid phase synthesis resin.

Dry loading: Dry resin is weighed (or measured by other means) and loaded directly into individual MicroKan™ reactors. This method is recommended for loading a relatively small number of MicroKan™ reactors.

Wet loading: A combination of two solvents with significantly differing densities, such as dichloromethane and hexane or dichloromethane and N,N-dimethylformamide (DMF) are used to suspend the resin. The first step is to determine the appropriate solvent ratio. Begin by placing a small amount of resin (50–100 mg) into a 10 mL graduated cylinder. Add 5 mL of methylene chloride and mix well. The resin will usually float. Slowly add small aliquots of hexane and mix well until the resin suspends in the mixture. Pipet the suspension of resin in the equal density mixture of methylene chloride and hexanes, into individual MicroKan™ reactors. Wet loading is recommended for loading a large number of MicroKans™.

Example of wet loading: If a total of 2.5 mL of hexane has been added to reach the suspension point, a mixture of methylene chloride/hexane in the ratio of 2:1 (v/v) can be used to suspend the resin. A suspension of 20–40 mg of resin per 1 mL of solvent mixture is recommended. If 20 mg of resin is to be loaded into each of 100 MicroKans™, 2 grams of resin is weighed and suspended in 50 mL of methylene chloride hexane (2:1). Using an additional 5 to 10% is recommended to allow for pipetting or other errors. Seat the MicroKans™ on top of the wells in a 96-deep well polypropylene microplate and pipet 0.5 mL of the resin suspension into each MicroKan™. The solvents will quickly drain into the wells and the loaded MicroKans™ can be capped and dried under vacuum. Moisture sensitive resin (such as trityl resin) is more safely loaded by the dry loading method.

The eight amino (TBDMS) protected alcohol derivatized resins 2a–h (FIGS. 1 and 2), are combined into four different mixtures (2a and 2b, 2c and 2d, 2e and 2f, and 2g and 2h). The four mixtures are separately wet loaded using an equal density mixture of dichloromethane and DMF into one of four groups of 500 MicroKans™ (30 mg resin/MicroKan™) each containing a radiofrequency (Rf) tag according to the procedure in Example 2. The MicroKans™ are washed and dried to give four groups of 500 MicroKans™, each group containing one of the above described sets of mixtures of resins and an Rf tag.

The MicroKans™ containing the mixtures of resins and Rf tags are recorded and assigned a code by the Synthesis Manager program and are sorted into ten different reaction flasks (10×200 MicroKans™). Each of the ten reaction flasks contains fifty copies of the four mixtures. The secondary amine of the (TBDMS) protected amino derivatized resins 2a–h (FIG. 1 and FIG. 2), are acylated by separately coupling the resins with five Fmoc-D-amino acids and five Fmoc-L-amino acids using bromo-tris-pyrrolidino phosphonium hexafluoro-phosphate (PyBroP) as the activating agent to give the products 3a–h (FIG. 1) as described in Example 3 (Coste, J.; Frerot, E.; Jouin, P., *Tetrahedron Lett.*, 1991, 32, 1967).

The Fmoc-D-amino acids and the Fmoc-L-amino acids utilized include but are not limited to following: N α-(9-fluorenylmethoxy carbonyl) O-tert-butyl-D-serine, N α-(9-fluorenylmethoxy carbonyl) O-tert-butyl-L-serine, N α-(9-fluorenylmethoxy carbonyl)-N γ-trityl-D-glutamine, N α-(9-fluorenylmethoxy carbonyl) N γ-trityl-L-glutamine, N α-(9-fluorenylmethoxy carbonyl) N γ-trityl-D-histidine, N α-(9-fluorenylmethoxy carbonyl) N γ-trityl-L-histidine, N α-(9-fluorenylmethoxy carbonyl) para-amino-(tert-butoxycarbonyl)-D-phenylalanine, N α-(9-fluorenyl methoxy carbonyl) para-amino-(tert-butoxycarbonyl)-L-phenylalanine, and N α-(9-fluorenylmethoxy carbonyl) N γ-(tert-butoxycarbonyl)-D-lysine, and N α-(9-fluorenylmethoxy carbonyl) N γ-(tert-butoxycarbonyl)-L-lysine.

Other Fmoc-D-amino acids and Fmoc-L-amino acids may be utilized for different embodiments of the invention. These include but are not limited to those derived from the naturally occurring amino acids and non-naturally occurring amino acids as previously described.

The Fmoc-D-amino acids and the Fmoc-L-amino acids are coupled to the (TBDMS) protected amino derivatized resins 2a–h (FIG. 1 and FIG. 2) using PyBroP activation to give the products 3a–h (FIG. 1) as described in Example 3. Due to the limited solubilities of their activated acids, the N α-(9-fluorenylmethoxy carbonyl) para-amino-(tert-butoxycarbonyl)-D and L-phenylalanines, are successfully coupled to the (TBDMS) protected amino derivatized resins 2a–h (FIG. 1 and FIG. 2) using 1,3-diisopropylcarbodiimide (DIC) as described in Example 4 (Angell, Y. M.; Garcia-Echeverria, C.; Rich, D. H., *Tetrahedron Lett.*, 1994, 35, 5981).

The coupling of an N-substituted amino acid is a difficult reaction in which the usual reagents are often inefficient (Coste, J.; Dufour, M. N.; Pantaloni, A.; Castro, B., *Tetrahedron Lett.*, 1990, 31, 669, Cheung, S. T.; Benoiton, N. L., *Can. J. Chem.*, 1997, 55, 911, Wenger, R. M.; *Helv. Chim. Acta.*, 1983, 66, 2672, Tung, R. D.; Rich, D. H., *J. Am. Chem. Soc.*, 1985, 107, 4342, Van der Auwera, C.; Anteunis, M. J. O., *Int. J. Peptide Protein Res.*, 1987, 29, 574). These N-substituted amino acid couplings are efficiently done with activated agents like PyBroP (bromo-tris-pyrrolidino phosphonium hexafluoro-phosphate) and PyCloP (chloro-tris-pyrrolidino phosphonium hexafluoro-phosphate) in high yields (>95%) and with minimal racemization (<0.3%) (Coste, J.; Frerot, E.; Jouin, P., *Tetrahedron Lett.*, 1991, 31, 1967). Similarly, the formation of an amide bond between an N-alkylated amine attached to a resin and the carboxyl group of an amino acid requires an activated coupling reagent like PyBroP or PyCloP or DIC. These reagents have the advantage of being stable, easy to use and are commercially available (Aldrich, Novabiochem (Switzerland)).

After coupling of the five Fmoc-D amino acids and the five Fmoc-L amino acids to the derivatized resin, all 2,000 of the MicroKans™ from the 10 reactions are combined for a common washing and drying as described in Example 5. The Fmoc protecting groups are removed by treatment of the 2,000 MicroKans™ with 20% piperidine in DMF for several hours to give the free amines as is described in Example 5 (Bodanszky, M.; Deshmane, S. S.; Martinez, J., *J. Org. Chem.*, 1979,44, 1622). The combined MicroKans™ are filtered, washed and dried.

Figure 7:
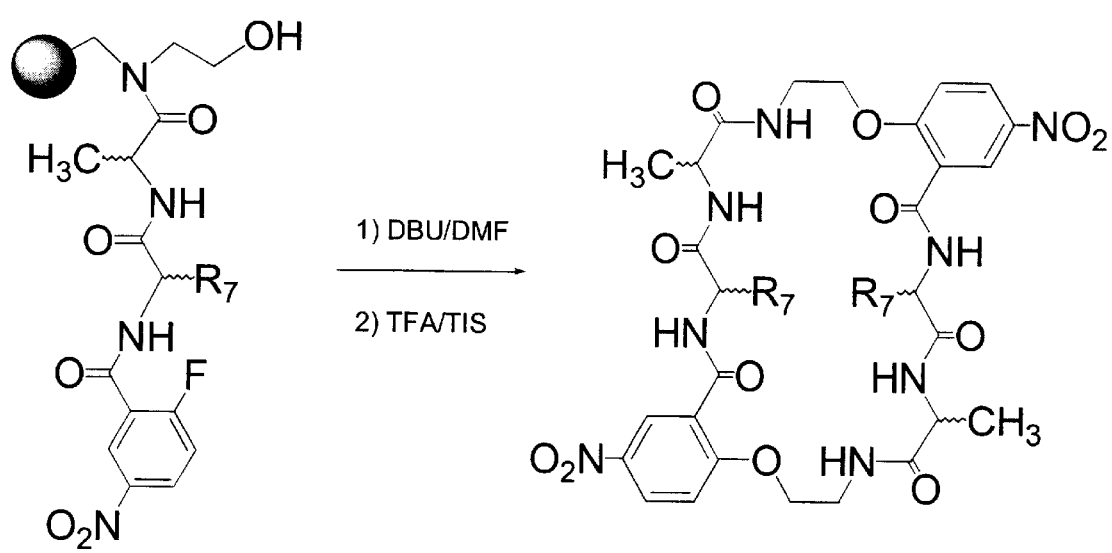
FIG. 7 is a schematic representation of a 26-membered dimerization product from solid phase synthesis.

The next coupling step is performed with β-amino acids. To achieve 14-membered macrocycles a β-amino acid is incorporated instead of an α-amino acid into the molecule to allow for the formation of a favorable 14-member macrocycle. The cyclization reaction with the β-amino acid N α-(9-fluorenylmethoxy carbonyl) β-alanine ($R_3$ and $R_4$=H) gives the desired 14 membered ring. The attempted cyclization, where an α-amino acid such as N α-(9-fluorenylmethoxy carbonyl)-glycine or N α-(9-fluorenylmethoxy carbonyl)-phenylalanine (FIG. 7) is incorporated into the chain gives a 26 membered cyclized dimer according to mass spectral analysis.

The five β-amino acids coupled to the amine derivatized resins include but are not limited to the following: N α-(9-fluorenylmethoxy carbonyl)-β-alanine, N α-(tert-butoxycarbonyl)-D,L-β-aspartic acid, (9-fluorenylmethoxy carbonyl)-D,L-2,3-diaminopropionic acid, N α-(9-fluorenylmethoxy carbonyl)-D,L-β-homoserine and N α-(9-fluorenylmethoxy carbonyl) O-tert-Butyl-D,L-β-homotyrosine. It should be noted that the β-amino acids described are used in the couplings as their D,L mixtures.

Prior to coupling with the five β-amino acids, the MicroKans™ (Rf tags) are read and sorted into five different reaction flasks (5×400 MicroKans™). Each of the five reaction flasks contains ten copies of the forty unique intermediate compounds which are bound to the resin as the described mixtures in the MicroKans™. The free amine derivatized resins are coupled to the five β-amino acids with O-(7-azabenzo-triazol-1-yl)-N,N,N',N'-tetramethyl-uronium hexafluorophosphate (HATU) and 2,4,6-collidine in DMF as described in Example 6 to give 4a-h (FIG. 1) (Marsh, I. R.; Bradley, M., *J. Org. Chem.*, 1997, 62, 6199).

The synthesis is flexible because virtually any α-amino acid can be converted into a β-amino acid by the Arndt-Eistert reaction (Guichard, G.; Abele, S.; Seebach, D., *Helv. Chem. Acta*, 1998, 81, 187). In the Arndt-Eistert synthesis a carboxylic acid is first converted into an α-diazo ketone. Subsequent rearrangement gives a carboxylic acid with one additional carbon atom (Meier; Zeller, Angew. Chem. Int. Ed. Engl. 1975, 14, 32, Angew. Chem. 87, 52. For a review of methods to synthesize β-amino acids see, *Enantioselective Synthesis of Beta-Amino Acids*, Juarish, E., John Wiley & Sons, New York, N.Y., 1997).

Other Fmoc-D,L-β-amino acids may be utilized for different embodiments of the invention. These include but are not limited to those derived from the naturally occurring amino acids and non-naturally occurring amino acids as previously described.

After coupling to the β-amino acids, all 2,000 of the MicroKans™ from the five reactions are combined for a common washing and deprotection of the Fmoc groups as described in Example 7. After washing and drying the MicroKans™, the Fmoc protecting groups are removed by treatment of the combined MicroKans™ with 20% piperidine in DMF for several hours to give the free amines (Bodanszky, M.; Deshmane, S. S.; Martinez, J., *J. Org. Chem.*, 1979,44, 1622). The MicroKans™ are filtered, washed and dried.

Prior to coupling with the $S_NAr$ cyclization linker, the MicroKans™ are sorted into two different flasks (2×1000 MicroKans™). The resin bound free amines are coupled to 2-fluoro-5-nitrobenzoic acid with O-(7-azabenzotriazol-1-yl)-N,N,N',N'-tetramethyluronium hexafluorophosphate (HATU) and 2,4,6-collidine in DMF as described in Example 8 to give 5a–h (FIG. 1).

Aromatic nucleophillic substitution ($S_NAr$) reactions are a useful way to effect cyclizations to give macrocyclic rings. Macrocyclic rings are 12 to 17 atoms in size. The mechanism for aromatic nucleophillic substitution consists of two steps. The initial attack by a nucleophile forms a bond with the aryl substrate, giving an intermediate, and then the leaving group departs. These reactions are successful because the aromatic ring is activated by an electron withdrawing group. In an $S_NAr$ reaction the substitutions are accelerated by electron withdrawing groups, especially in positions ortho and para to the leaving group and hindered by electron donating groups. The effect of meta substituents has been studied much less, but it has been reported that here too, electron withdrawing groups increase the rate (Nurgatin; Sharmin, Ginzburg, *J. Org. Chem. USSR*, 1983, 19, 343).

Recently, several examples of the $S_NAr$ cyclization reaction on a solid support that are useful for the synthesis of β-turn libraries have been reported (Feng, Y.; Wang, Z.; Jin, S.; Burgess, K., *J. Am. Chem. Soc.*, 1998, 120, 10768, Kiselyov, A. S.; Eisenberg, S.; Luo, Y., Tetrahedron, 1998, 54, 10635). For selected publications on $S_NAr$ see, for example: Ouyang, X.; Tamayo, N.; Kiselyov, A. S., Tetrahedron, 5 1999, 55, 2827, Rama Rao, A. V.; Gurjar, M. K,; Lakshmipathi, P.; Reddy, M. M.; Nagarajan, M.; Shashwati Pal; Sarma, B. V. N. B. S.; Tripathy, N. K., *Tetrahedron Lett.*, 1997, 38(42), 7433,Rama Rao, A. V.; Gurjar, M. K,; Reddy, K. L.; Rao, A. S., Chem. Rev., 1995, 95, 2135, Beugelmans, R.; Zhu, J.; Husson, N.; Bois-Choussy, M.; Singh, G. P., *J. Chem. Soc., Chem. Commun.*, 1994, 439, Terrier, F., *Nucleophillic Aromatic Displacement: The Role of the Nitro Group*; VCH: New York, 1991, Chapter 1, Artamkina, G. A.; Egorov, M. P.; Beletskaya, I. P., *Chem. Rev.*, 1982, 82, 427, Paradisi, C., *Arene Substitution via Nucleophilic Addition to Electron Deficient Arenes. Comprehensive Organic Synthesis*; Trost, B. M.; Fleming, I, Eds. Pergamon Press: Oxford, 1991, Vol 4, 423.

Before TBDMS deprotection of the primary alcohol, the MicroKans™ are divided into two different flasks (2×1000 MicroKans™). The TBDMS group is then removed by treatment of the MicroKans™ containing the resin with triethylamine trihydro fluoride (TREAT-HF) in THF according to the procedure as described in Example 9 (for a review of TREAT-HF, see *Aldrichimica Acta*, 1995, 28, 31).

After washing and drying, the MicroKans™ are divided into two flasks (2×1000). Cyclization is effected by swirling the MicroKans™ in a solution of 1,8-diazabicyclo [5.4.0] undec-7-ene (DBU) in DMF for three days as described in Example 10. The cyclization products are the 14 membered rings 6a–h where $R_5$=$NO_2$(FIG. 1). The MicroKans™ are combined, washed and dried as described in Example 10.

The aryl nitro group is an important latent combinatorial diversity site as it can be reduced to the amine and subsequently functionalized with a collection of RNA-binding carboxylic acids. Following DBU induced $S_NAr$ macrocyclization, the nitro group of the resin bound structures are reduced with tin (II) chloride ($SnCl_2$) (Wei, G. P.; Phillips, G. B., Tetrahedron Lett., 1998, 39, 179). The MicroKans™ are divided into two flasks (2×1000) and treated with a solution of $SnCl_2$ in DMF to reduce the nitro group to the corresponding amines as described in Example 11. The MicroKans™ are then combined and washed and dried.

The MicroKans™ (Rf tags) are read and sorted into ten different reaction flasks (10×200 MicroKans™). Each of the ten reaction flasks contains one copy of the two hundred unique intermediate compounds which are bound to the resin as the described mixtures in the MicroKans™. One set of the 200 MicroKans™ are cleaved directly from the resin with trifluoroacetic acid and triethylsilane to afford the macrocyclic amines 7a–h where $R_5$ is $NH_2$ (FIG. 1) as described in Example 12. The remaining nine sets of MicroKans™ are reacted with either a carboxylic acid or an isocyanate to form a carboxamide (amide) as described in Examples 13, 14 and 15.

Eight carboxylic acids are coupled to the amine derivatized resin 7a–h, to form an amide as shown in FIG. 1. A general procedure for the acylation of the amine derivatized resins 7a–h where $R_5$ is $NH_2$ (FIG. 1) with a carboxylic acid is given in Example 13. As previously described, HATU is an effective reagent for amide bond formation on solid phase. The carboxylic acids utilized include but are not limited to the following: O-(tert-butoxycarbonyl)-acetic acid, 3-({[4-methoxyphenylmethyl] amino}carbonylamino) benzoic acid, 2,3-dihydroxyquinoxaline-6-carboxylic acid, hydantoic acid, N-(tert-butoxycarbonyl)-isonipecotic acid, nalidixic acid, N-(tert-butoxycarbonyl)-O-tert-butyl-L-serine and thymine-1-acetic acid.

Due to the low solubility of the activated intermediates, an alternative coupling procedure for nalidixic acid is given in Example 14. The coupling is accomplished by the addition of excess HATA and diiso-propylethylamine (DIEA) to the reaction mixture.

An amide bond can also be formed by the reaction of an amine with an isocyanate. Treatment of the amine derivatized resin 7a–h where $R_5$ is $NH_2$ (FIG. 1) with 4-methoxybenzylisocyanate gives the corresponding amide as described in Example 15.

It should be noted that the above described amino acids, carboxylic acids and isocyanates contain various protecting groups that are acid sensitive. These protecting groups include: N-tert-butoxycarbonyl (t-BOC), 2,2,5,7,8-pentamethylchroman-6-sulfonyl (Pmc), triphenylmethyl (trityl), O-tert-butoxycarbonyl (t-BOC), O-tert-butyl ethers (t-bu) and [4-(methoxy)phenyl]methyl or (para-methoxybenzyl). These acid sensitive protecting groups are removed upon exposure to trifluoroacetic acid during cleavage of the 14-membered macrocycles from the resin to give their corresponding amine, amidinoamino, carboxamide, carboxy, alcohol and urea groups, respectively.

The nine sets of MicroKans™ are combined for a common washing and drying. Before cleavage from the resin, each of the MicroKans™ (Rf tags) are read and are sorted into a 96 well plate format. Each of the 2,000 MicroKans™ now contains one copy of a mixture of two unique molecular weights of up to eight resin bound compounds.

The compounds synthesized can be cleaved directly from the MicroKans™ without the need to open the them. However, the presence of a small number of resin beads smaller than the mesh opening is inevitable due to the size distribution of the commercial resin and the mechanical actions during the synthetic procedures, which tend to break resin beads to a certain degree. Therefore, a filtration is recommended after the cleavage. Alternatively, a disposable Microreactor Carrier can be used where each well in the 96-position carrier incorporates a 0.5 mm polyethylene filter for restraining the passage of any resin fines after cleaving.

Typical cleavage conditions for ArgoGel™-MB-CHO resin include activation with an isocyanate, sulfonyl chloride or acyl derivative followed by treatment with 95:5 trifluoroacetic acid:water or 95:5 trifluoroacetic acid:triisopropylsilane.

Each of the 2,000 MicroKans™ were washed twice with 1.8 mL of a solution containing 95% trifluoroacetic acid and 5% triisopropylsilane as described in Example 16 to give the 14 membered macrocycles 7a–h where $R_5$ is NHCOR as a mixture of two compounds (FIG. 1). The cleaved 14 membered macrocyclic rings are filtered, evaporated, diluted with dioxane and water, evaporated and dried under high vacuum.

The embodiments of the invention described are for a process to make macrocyclic rings to give either mixtures or to give pure compounds. A 2,000 member library of macrocyclic compounds is synthesized using the above described procedures. The substituents $R_1$, $R_2$, $R_3$, $R_4$, and $R_5$ are as shown in FIGS. 2–6, respectively. The resultant mixtures from the 2,000 MicroKans™ are screened for their antimicrobial activity.

TABLE 1

14-Membered Macrocycles.

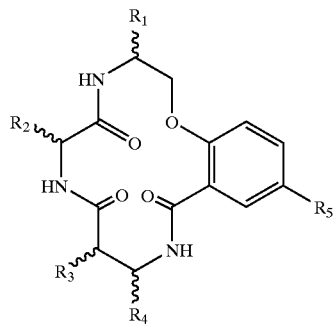

|   | $R_1$ | $R_2$ | $R_3/R_4$ | $R_5$ | MS-EI, M + H | HPLC* (%) |
|---|---|---|---|---|---|---|
| 1 | H | methyl | H | — | 351 | 95 |
| 2 | methyl | hydroxyl methyl | amine | — | 396 | 97 |
| 3 | methyl | isobutyl | amine | — | 422 | 98 |
| 4 | 3-amidino amino propyl | carboxamide methyl | H | 2-pyrazine carboxyl | 569 | 84 |
| 5 | 3-amidino amino propyl | isobutyl | H | carboxamide | 505 | 85 |
| 6 | methyl | 2-carboxy ethyl | amine | isonipecotyl | 519 | 82 |
| 7 | hydroxyl methyl | benzyl | carboxy | isonipecotyl | 582 | 92 |

TABLE 1-continued

14-Membered Macrocycles.

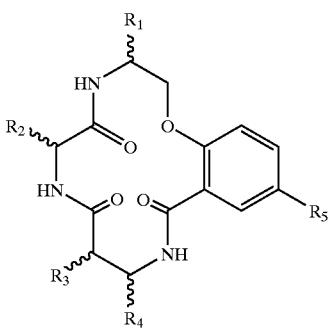

| | R₁ | R₂ | R₃/R₄ | R₅ | MS-EI, M + H | HPLC* (%) |
|---|---|---|---|---|---|---|
| 8 | hydroxyl methyl | isobutyl | amine | 2-pyrazine carboxyl | 514 | 93 |
| 9 | 4-hydroxyl benzyl | benzyl | H | isonipecotyl | 614 | >95 |
| 10 | hydroxyl methyl | isobutyl | amine | thymine-1-acetyl | 574 | 78 |
| 11 | 4-amino butyl | carboxamide methyl | H | 2-pyrazine carboxyl | 541 | 77 |
| 12 | 3-amidino amino propyl | isobutyl | amine | 2-pyrazine carboxyl | 583 | 89 |
| 13 | 4-amino butyl | isobutyl | amine | thymine-1-acetyl | 615 | 91 |
| 14 | 4-hydroxyl benzyl | carboxamide methyl | amine | thymine-1-acetyl | 651 | 82 |
| 15 | methyl | 3-amidino amino propyl | amine | thymine-1-acetyl | 601 | 75 |
| 16 | 4-amino butyl | benzyl | H | thymine-1-acetyl | 634 | 93 |
| 17 | 4-amino butyl | carboxamide methyl | H | thymine-1-acetyl | 601 | 65 |
| 18 | methyl | isobutyl | carboxy | isonipecotyl | 532 | 79 |
| 19 | 4-amino butyl | 2-carboxy ethyl | H | 2-pyrazine carboxyl | 556 | 73 |
| 20 | 4-hydroxyl benzyl | benzyl | carboxy | isonipecotyl | 658 | 89 |
| 21 | methyl | isobutyl | amine | carboxamide | 435 | 98 |
| 22 | 4-amino butyl | isobutyl | H | carboxamide | 477 | 76 |
| 23 | 4-amino butyl | hydroxyl methyl | H | carboxamide | 451 | 93 |
| 24 | 4-amino butyl | hydroxyl methyl | H | thymine-1-acetyl | 574 | 80 |
| 25 | 4-hydroxyl benzyl | benzyl | carboxy | 2-pyrazine carboxyl | 653 | 81 |
| 26 | hydroxyl methyl | isobutyl | carboxy | isonipecotyl | 548 | 72 |
| 27 | 3-amidino amino propyl | hydroxyl methyl | amine | thymine-1-acetyl | 617 | 91 |

*Reverse-phase HPLC employed an evaporative light-scattering detector (SEDEX). In some cases the macrocyclic diastereomers were not HPLC-resolved and purities reflect the sum of two peaks.

Included within the scope of the present invention are the pharmaceutically acceptable salts of the foregoing compounds. As used herein, the term "pharmaceutically acceptable salts" refers to non-toxic acid addition salts and alkaline earth metal salts of the compounds of the invention. The salts can be prepared in situ during the final isolation and purification of the compounds of the invention, or separately by reacting the free base or acid functions with a suitable organic acid or base. Representative acid addition salts include the hydrochloride, hydrobromide, sulphate, bisulphate, acetate, oxalate, valerate, oleate, palmitate, stearate, laurate, borate, benzoate, lactate, phosphate, tosylate, mesylate, citrate, maleate, fumarate, succinate, tartrate, glucoheptonate, lactobionate, lauryl sulfate salts and the like. Representative alkali or alkaline earth metal salts include the sodium, calcium, potassium and magnesium salts, etc.

Another aspect of the invention is a method for inhibiting the growth or reproduction of disease-causing microorganisms. A process is described for destroying or inhibiting the growth or reproduction of disease-causing microorganisms comprising treating the disease-causing microorganisms with a compounds of the invention.

It has been found that the compounds of the present invention possess antibacterial activity against a wide spectrum of gram positive and gram negative bacteria, as well as enterobacteria and anaerobes. The compounds of the invention are therefore useful in the antibiotic treatment of susceptible bacterial infections in both humans and animals. In addition, the compounds, by reason of their in vitro activity, may be used in scrub solutions for surface inhibition of bacterial growth or as an additive to laundering compositions.

Susceptible organisms generally include those gram positive and gram negative, aerobic and anaerobic organisms whose growth can be inhibited by the compounds of the invention such as Staphylococcus, Lactobacillus, Streptococcus, Sarcina, Escherichia, Enterobacter, Klebsiella, Pseudomonas, Acinetobacter, Proteus, Campylobacter, Citrobacter, Nisseria, Baccillus, Bacteroides, Peptococcus, Clostridium, Salmonella, Shigella, Serratia, Haemophilus, Brucella and other organisms.

The compounds of the invention are particularly useful for treating microbial infections such as *K. pneumoniae, E. coli, s. aureus, E. faecalis* and *M. tuberculosis*.

Accordingly there is provided a method of treating bacterial infection in a mammal comprising administering to the mammal, for example a human, an effective amount of a compound of the invention. By "effective amount" is meant an amount of compound which upon administration is capable of reducing or preventing proliferation of the bacteria or reducing or preventing symptoms associated with the bacterial infection. The actual amount of compound administered and the route of administration will depend upon the particular disease or bacteria as well as other factors such as the size, age, sex and ethnic origin of the individual being treated and is determined by routine analysis. The compounds of the invention may also be formulated into compositions together with pharmaceutically acceptable carriers for parenteral injection, for oral administration in solid or liquid form, for rectal administration, and the like. In methods of the invention, the compound may be administered orally (including buccal, sublingual, inhalation), nasally, rectally, vaginally, intravenously, intradermally, subcutaneously and topically. Compounds will be formulated into compositions suitable for administration for example with suitable carriers, diluents, thickeners, adjuvants, etc. As are routine in the formulation art. Compositions of the invention may also include additional active ingredients. Dosage forms include solutions, powders, tables, capsules, gel capsules, suppositories, topical ointments and creams and aerosols for inhalation.

Formulations for non-parenteral administration may include sterile aqueous solutions which may also contain buffers, diluents and other suitable additives. Pharmaceutically acceptable organic or inorganic carrier substances suitable for non-parenteral administration which do not deleteriously react with compounds of the invention can be used. Suitable pharmaceutically acceptable carries include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like. The formulations can be sterilized and, if desired, mixed with auxiliary agents, e.g., lubricants, preservatives, stabilizers, wetting agents, emulsifiers, salts for influencing osmotic pressure, buffers, colorings flavorings and/or aromatic substances and the like which do not deleteriously react with compounds of the invention. Aqueous suspensions may contain substances which increase the viscosity of the suspension including, for example, sodium carboxymethylcellulose, sorbitol and/or dextran. Optionally, the suspension may also contain stabilizers.

In a preferred embodiment, compounds of the invention are administered via oral delivery. Compositions for oral administration include powders or granules, suspensions or solutions in water or non-aqueous media, capsules, sachets, troches, tablets or SECs (soft elastic capsules or caplets). Thickeners, flavoring agents, diluents, emulsifiers, dispersing aids, carrier substances of binders may be desirably added to such formulations. The use of such formulations has the effect of delivering the nucleic acid to the alimentary canal for exposure to the mucosa thereof. Accordingly, the formulation can consist of material effective in protecting the compound from pH extremes of the stomach, or in releasing the compound over time, to optimize the delivery thereof to a particular mucosal site. Enteric coatings for acid-resistant tablets, capsules and caplets are known in the art and typically include acetate phthalate, propylene glycol and sorbitan monoleate.

Various methods for producing formulations for alimentary delivery are well known in the art. See, generally, Nairn, Chapter 83; Block, Chapter 87; Rudnic et.al., Chapter 89; and Longer et. al., Chapter 91 In: Remington's Pharmaceutical Sciences, 18$^{th}$ Ed., Gennaro, ed., Mack Publishing Co., Easton, Pa., 1990. The formulations of the invention can be converted in a known manner into the customary formulations, such as tablets, coated tablets, pills, granules, aerosols, syrups, emulsions, suspensions and solutions, using inert, non-toxic, pharmaceutically suitable excipients or solvents. The therapeutically active compound should in each case be present in a concentration of about 0.5% to about 95% by weight of the total mixture, that is to say in amounts which are sufficient to achieve the desired dosage range. The formulations are prepared, for example, by extending the active compounds with solvents and/or excipients, if appropriate using emulsifying agents and/or dispersing agents, and, for example, in the case where water is used as the diluent, organic solvents can be used as auxiliary solvents if appropriate.

Compositions may be formulated in a conventional manner using additional pharmaceutically acceptable carriers or excipients as appropriate. Thus, the composition may be prepared by conventional means with additional carriers or excipients such as binding agents (e.g., pregelatinised maize starch, polyvinylpyrrolidone or hydroxypropyl methylcellulose); filters (e.g., lactose, microcrystalline cellulose or calcium hydrogen phosphate); lubricants (e.g., magnesium stearate, talc or silica); disintegrates (e.g., starch or sodium starch glycolate); or wetting agents (e.g., sodium lauryl sulfate). Tablets may be coated by methods will known in the art. The preparations may be also contain flavoring, coloring and/or sweetening agents as appropriate.

The pharmaceutical formulations, which may conveniently be presented in unit dosage form, may be prepared according to conventional techniques well known in the pharmaceutical industry. Such techniques include the step of bringing into association the active ingredients with the pharmaceutical carrier (s) or excipient (s). In general the formulations are prepared by uniformly and intimately bringing into association the active ingredients with liquid carriers or finely divided soled carriers or both, and then, if necessary, shaping the product.

Formulations of the present invention suitable for oral administration may be presented as discrete units such as capsules, cachets or tables each containing predetermined amounts of the active ingredients; as powders or granules; as solutions or suspensions in an aqueous liquid or a non-aqueous liquid; or as oil-in-water emulsions or water-in-oil liquid emulsions. A tablet may be made by compression or molding, optionally with one or more accessory ingredients. Compressed tablets may be prepared by compressing in a suitable machine, the active ingredients in a free-flowing form such as a powder or granules, optionally mixed with a binder, lubricant, inert diluent, preservative, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredients therein.

EXAMPLES

General

Reagents and solvents are purchased from either Aldrich Chemicals, Bachem or CalBiochem. Combinatorial apparatuses and equipment are purchased from IRORI. Reactions are performed under an argon atmosphere unless otherwise noted. Column chromatography is carried out using normal phase silica gel. Solvent ratios are given as volume/volume. Solvent gradients are carried out step-wise. Evaporations of solvents are performed in vacuo (50 torr) at 35° C. unless otherwise specified. NMR spectra are obtained with the following instruments: $^1$H NMR: Varian Gemini-200 (199.975 MHZ) or Varian Unity 400 (399.952 MHZ). $^{13}$C NMR: Varian Gemini-200 (50.289 MHZ). $^{31}$P NMR: Varian Gemini-200 (79.990 MHZ). NMR spectra are recorded using either deuteriochloroform, dimethylsulfoxide-d$_6$, dimethylformamide-d$_7$, or deuteriomethanol as solvent (tetramethylsilane as internal standard). The following abbreviations are used to designate the multiplicity of individual signals: s=singlet, d=doublet, t=triplet, q=quartet, m=multiplet, dd=doublet of doublets, br s=broad singlet. Mass spectra are performed by Mass Consortium, San Diego, Calif.

Example 1a (2a–d, f, g) (FIG. 1, Steps a, b, and c)

To a reaction flask containing the Fmoc-D,L-amino alcohol (15 mmol) is added methanol(MeOH) (90 mL) followed by sodium methoxide (6.5 mL, 30 mmol, 25% wt. in methanol). The reaction is swirled for 4–5 h on an orbital shaker. Acetic acid (1.89 mL, 33 mmol) is added and the reaction is left swirling for 30 min. Trimethylorthoformate (60 mL) is added followed by ArgoGel-MB-CHO resin (30 g, 12 mmol). Additional methanol is added to keep the resin wet (80–100 mL) and the reaction is swirled overnight. The next day pyridine-borane (3.8 mL, 30 mmol, 8 M) and acetic acid (1.8 mL, 30 mmol) are added and the reaction is left swirling overnight. The following day the resin is filtered and washed with MeOH, DMF, dichloromethane (DCM), and MeOH (each 3×2,000 mL). The resin is dried under high vacuum over $P_2O_5$. The primary alcohol of the amino alcohol-derivatized resin (ca. 30 g, ca. 10 mmol) is protected by suspending the resin in DCM (ca. 250 mL) followed by the addition of TBDMS-Cl (8.7 g, 58 mmol), triethylamine (8 mL, 58 mmol) and DMAP (2.3 g, 19 mmol). The reaction is left swirling on the orbital shaker overnight. The next day the resin is filtered and washed with DCM, DMF and MeOH (each 3×2,000 mL). The resin is dried under high vacuum over $P2O_5$.

Example 1b
(2e, 2h) (FIG. 1, Steps b and c)

To the amino alcohol is added MeOH (ca. 150 mL) and trimethylorthoformate (39 mL) followed by ArgoGel-MB-CHO resin (30 g). The reaction is left swirling overnight. The next day pyridine-borane (8 M, 11.6 mL, 93 mmol) and acetic acid (5.3 mL, 93 mmol) are added. Additional MeOH is added to keep the resin wet. The reaction is left swirling overnight. The following day the resin is filtered and washed with MeOH, DMF, DCM and MeOH (each 3×2,000 mL). The resin is dried under high vacuum over $P_2O_5$. The hydroxyl group of the amino alcohol-derivatized resin (ca. 30 g, ca. 10 mmol) is protected by suspending the resin in DCM (ca. 250 mL) followed by the addition of TBDMS-Cl (8.7 g, 58 mmol), triethylamine (8 mL, 58 mmol) and DMAP (2.3 g, 19 mmol). The reaction is left swirling on the orbital shaker overnight. The next day the resin is filtered and washed with DCM, DMF and MeOH (each 3×2,000 mL). The resin is dried under high vacuum over $P_2O_5$.

Example 2
(FIG. 1, Step d)

The radiofrequency (Rf) tags are sorted into four groups (4×500 tags) and loaded into 2,000 MicroKans™. The amino alcohol-derivatized resins 2a–h are loaded into the appropriate MicroKans™ using an equal density mixture of DCM and DMF. Four different mixtures (1a and 1b, 1c and 1d, 1e and 1f, 1g and 1h) of two amino alcohol-derivatized resins are loaded into the MicroKans™ (30 mg resin/MicroKan™). The MicroKans™ are washed with DCM (2×2,000 mL) and MeOH (2×2,000 mL) and dried under high vacuum over $P_2O_5$.

Example 3
(3a–h) (FIG. 1, Step d Continued)

Prior to these coupling reactions, the resins are sorted into 10 reaction flasks (10×200 MicroKans™). The Fmoc-D,L amino acids are reacted separately. The acylations are carried out with Fmoc-D-Ser (tBu)-OH, Fmoc-L-Ser(tBu)-OH, Fmoc-D-Gln(Trt)-OH, Fmoc-L-Gln(Trt)-OH, Fmoc-D-His (Trt)-OH, Fmoc-L-His(Trt)-OH, and Fmoc-p-amino(Boc)-D-Phe-OH, Fmoc-p-amino(Boc)-L-Phe-OH, N-Fmoc-N-Boc-D-aminobutyric acid and N-Fmoc-N-Boc-L-aminobutyric acid.

All amino acids are reacted using PyBroP activation, except for Fmoc-p-amino(Boc)-Phe. To a flask is added PyBroP (23 g, 0.25 mol) followed by DCM (183 mL) and DIEA (17 mL, 0.5 M). The Fmoc-protected amino acid (50 mmol, 0.25 M) is added followed by 200 MicroKans™. A vacuum is applied to the flask followed by a flow of argon gas to remove the air pockets in the MicroKans™. The flask is allowed to swirl overnight on the orbital shaker. The solvent is removed and the MicroKans™ are washed with DMF (3×2,000 mL)

Example 4
(3a–h) (FIG. 1, Step d Continued)

To a reaction flask is added Fmoc-p-amino(Boc)Phe (40 mmol, 0.2 M) followed by DMF (194 mL) and diisopropyl-carbodiimide (DIC) (6.3 mL, 0.2 M). To the solution is added 200 MicroKans™. A vacuum is applied to the flask followed by a flow of argon gas to remove the air pockets in the MicroKans™. The solvent is removed and the MicroKans™ are washed with DMF (3×2,000 mL).

Example 5
(FIG. 1, Step e)

All MicroKans™ from the 10 reactions are combined for a common washing step. They are washed with DMF, DCM, DMF, DCM and MeOH (each 3×2,000 mL). The MicroKans™ are then dried in a vacuum oven over $P_2O_5$. All the MicroKans™ are then treated with 20% piperidine/DMF for 3–4 hours. The MicroKans™ are then filtered and washed with DMF, DCM, DMF, DCM and MeOH (each 3×2,000 mL). The MicroKans™ are dried in a vacuum oven over $P_2O_5$.

Example 6
(4a–h) (FIG. 1, Step f)

Prior to the reaction with the β-amino acids, the MicroKans™ are sorted into 5 different flasks (5×400 MicroKans™). The following 5-amino acids are reacted: Fmoc-β-Ala, N-β-Boc-N-β-Fmoc-D,L-diaminopropionic acid, Fmoc-D,L-β-homo-Ser, Fmoc-D,L-β-homo-Tyr (OtBu)-OH, and Fmoc-D,L-Asp(OtBu). To a flask is added HATU (16.7 g, 44 mmol, 0.11 M), the Fmoc-β-amino acid (0.11M, 44 mmol, 0.11M) and DMF (390 mL) followed by collidine (13.2 mL, 100 mmol, 0.25 M). To this solution is added 400 MicroKans™. A vacuum is applied to the flask followed by a flow of argon gas to remove the air pockets in the MicroKans™. The reactions are left swirling on the orbital shaker overnight. The next day the solvent is removed and the MicroKans™ from each reaction are washed separately with DMF (3×2,000 mL).

Example 7
(FIG. 1, Step g)

All of the MicroKans™ from the 10 reactions are combined for a common washing step with DMF, DCM, DMF, DCM and MeOH (each 3×2,000 mL) and are dried in a vacuum oven over $P_2O_5$. The MicroKans™ are treated with 20% piperidine/DMF (2,000 mL) for 3–4 hours and are washed with DMF, DCM, DMF, DCM and MeOH (each 3×2,000 mL). The MicroKans™ are dried in a vacuum oven over $P_2O_5$.

Example 8
(5a–h) (FIG. 1, Step h)

To two reaction flasks are added 2-fluoro-5-nitrobenzoic acid (19 g, 0.11 M), HATU (42 g, 0.11 M), DMF (500 mL) and DCM (500 mL). Collidine (29 mL, 0.22 M) is added followed by the addition of 1,000 MicroKans™ to each flask. A vacuum is applied to the flask followed by a flow of argon gas to remove the air pockets in the MicroKans™. The flasks are then allowed to swirl overnight on the orbital shaker. The solvent is removed and the MicroKans™ are combined and washed with DMF, DCM, DMF, DCM and MeOH (each 3×2,000 mL). The MicroKans™ are dried in a vacuum oven over P₂O₅.

Example 9
(FIG. 1, Step i)

A solution of TREAT-HF (34 mL, 0.2 M) in THF (966 mL) is added to two reaction flasks each containing 1,000 MicroKans™. The flasks are allowed to swirl overnight on the orbital shaker. The solvent is removed and the MicroKans™ are combined and washed with DMF, DCM, DMF, DCM and MeOH (each 3×2,000 mL). The MicroKans™ are dried in a vacuum oven over P₂O₅ for 2 days.

Example 10
(6a–h) (FIG. 1, Step j)

To two reaction flasks each containing a solution of DBU (30 mL, 0.2 M) in DMF is added 1,000 MicroKans™ (2×1,000 MicroKans™). The reaction flasks are allowed to swirl for 3 days. The solvent is removed and the MicroKans™ are combined and washed DMF, DCM, DMF, DCM and MeOH (each 3×2,000 mL). The MicroKans™ are dried in a vacuum oven over P₂O₅.

Example 11
(6a–h) (FIG. 1, Step k)

A solution of SnCl₂ (285 g, 1.5 M) in DMF is added to each of two reaction flasks. 1,000 MicroKans™ (2×1,000 MicroKans™) are added to each flask and the flasks are allowed to swirl overnight over an atmosphere of Argon. The solvent is removed and the MicroKans™ are washed with isopropanol (IPA), DCM, IPA, CHCl₃, DMF and MeOH (each 3×2,000 mL). The MicroKans™ are dried under high vacuum over P₂O₅.

Example 12
(6a–h) (FIG. 1, Step m)

The MicroKans™ are sorted into 10 reaction flasks (10× 200 MicroKans™). One set of 200 MicroKans™ is set aside to give the amine. The remainder of the MicroKans™ (8×200 MicroKans™) are reacted with 8 carboxylic acids: [Boc-Ser(tBu)-OH, 3-({[4-methoxyphenylmethyl]amino}carbonylamino)benzoic acid, hydantoic acid, tert-butoxyacetic acid, Boc-isonipecotic acid, thymine-1-acetic acid, 2,3-dihydroxy-quinoxaline-6-carboxylic acid)] as described in Example 13, and with nalidixic acid as described in Example 14. The remainding set of MicroKans™ are reacted with 4-methoxy-benzylisocyanate as described in Example 15.

Example 13
(6a–h) (FIG. 1, Step m)

A carboxylic acid (22 mmol, 0.11M), HATU (8.4 g, 22 mmol, 0.11M) and DMF (194 mL) is added to a reaction flask followed by collidine (6.6 mL, 50 mmol, 0.25M). To this solution is added 200 MicroKans™. The reaction is allowed to proceed overnight. The solvent is removed and the MicroKans™ are washed with DMF (3×2,000 mL). The MicroKans™ from the 7 reactions are combined for a common washing step with DMF, DCM, DMF, DCM and MeOH (each 3×2,000 mL). The MicroKans™ are dried in a vacuum oven over P₂O₅.

Example 14
(6a–h) (FIG. 1, Step m)

To a solution of nalidixic acid (5.1 g, 22 mmol, 0.11 M) and HATU (8.4 g, 22 mmol, 0.11 M) is added DMF (185 mL), collidine (6.6 mL, 50 mmol, 0.25 M) and DIEA (8.7 mL, 50 mmol, 0.25 M). To this solution is added 200 MicroKan™. The reaction is allowed to proceed overnight whereupon a solid precipitated out of solution. The next day the MicroKans™ are filtered and washed with DMF, DCM, IPA, MeOH, DCM and MeOH (each 3×2,000 mL). The MicroKans™ are then dried under high vacuum over P₂O₅. The reaction with nalidixic acid was repeated a second time along with the washing steps.

Example 15
(6a–h) (FIG. 1, Step m)

To a solution of 4-methoxybenzylisocyanate (5.7 mL, 40 mmol, 0.2 M) in DMF (195 mL) is added 200 MicroKans™. The reaction is allowed to proceed overnight. The next day the MicroKans™ are filtered and washed with DMF (3×200 mL). The MicroKans™ are then combined with those that were reacted with carboxylic acids for a common washing step as described above.

Example 16
(7a–h) (FIG. 1, Step l)

After each MicroKan™ was archived into a 96-well plate format, it was washed with 1.8 mL of 95% trifluoroacetic acid/5% triisopropylsilane. The volatiles were removed under vacuum and 0.5 mL of dioxane/H₂O (1:1), was added to each well. The volatiles were removed under vacuum and the compounds dried under high vacuum over P₂O₅.

The Mass Spectral (MS) and purity data for a representative set of compounds (5×6×3×4) is summarized in Table 1. NMR data was obtained on single compound samples (1 and 2 as shown in Table 1), whose synthesis was carried out separately on a 100 mmol scale. The compounds were prepared using L-Fmoc-alaninol as the amino alcohol component ($R_1$)

1: $^1$H NMR (400 MHz, dmso-$d_6$) 8.78 (d, 1H, J=6.0 Hz), 8.70 (s, 1H), 8.30–8.39 (m, 3H), 8.18 (br s, 2H), 7.82 (d, 1H, J=6.0 Hz), 7.53 (d, 1H, J=9.6 Hz), 5.10 (br s, 1H), 4.33–4.40 (m, 3H), 4.01–4.03 (m, 1H), 4.08–4.13 (m, 2H), 3.95–3.98 (m, 2H), 3.64–3.66 (m, 2H), 1.18 (d, 3H, J=7 Hz) ppm. $^{13}$C NMR (100 MHz, dmso-$d_6$) 169.74, 166.92, 164.00, 160.93, 140.96, 128.32, 126.90, 122.35, 114.83, 70.74, 69.78, 60.56, 58.29, 52.64, 40.13, 16.66 ppm.

2: $^1$H NMR (400 MHz, dmso-$d_6$) 8.71 (s, 1H), 8.52 (d, 1H, J=6.0 Hz), 8.38 (d, 1H, J=9.2 Hz), 8.23–8.31 (m, 3H), 7.86 (d, 1H, J=6 Hz), 7.53 (d, 1H, J=9.6 Hz), 4.40–4.45 (m, 1H), 4.35–4.31 (m, 1H), 4.09–4.12 (m, 2H), 3.98 (m, 1H), 3.90–3.94 (m, 2H), 1.43–1.67 (m, 3H), 1.18 (d, J=6.8 Hz), 8.75 (dd, 6H)ppm. $^{13}$C NMR (100 MHz, dmso-$d_6$) 171.83, 166.64, 163.79, 160.99, 140.94, 128.34, 126.97, 122.22, 114.74, 70.71, 69.77, 53.65, 52.42, 44.47, 24.11, 22.72, 21.45, 16.42 ppm.

Example 17
In Vitro Antibacterial Activity Determination of Minimum Inhibitory Concentrations (MICs).

The assays are carried out in 150 µL volume in duplicate in 96-well clear flat-bottom plates. The bacterial suspension from an overnight culture growth in appropriate medium is added to a solution of test compound in 4% DMSO in water. Final bacterial inoculum is approximately $10^5$–$10^6$ CFU/well. The percent growth of the bacteria in test wells relative to that observed for a well containing no compound is determined by measuring absorbance at 595 nm ($A_{595}$) after 24 h. The MIC is determined as a range of single compound where the complete inhibition of growth is observed at the higher concentration and cells are viable at the lower concentrations. Both ampicillin and tetracycline are used as antibiotic-positive controls in each screening assay for *S. pyogenes, E. coli imp-, E. coli, S. aureus, E. faecalis, K.*

*pneumoniae* and *P. vulgaris*. Ciprofloxacin is used as an antibiotic positive control in each screening assay for *P. aeruginosa*.

Animal and in Vivo Studies.

Male ICR mice are fed with autoclaved commercial food pellets and sterile water ad libitum. Animals are inoculated intraperitoneally with $8.0 \times 10^6$ CFU/0.5 mL/mouse of *K. pneumoniae* (ATCC 10031) in BHI containing 5% mucin. Ten animals each are randomly assigned to either control or treatment groups. Test compound and gentamycin (included as a positive control) are both administered subcutaneously one hour after infection. Test compound is administered as a solution in DMSO (100%) and 50 µL/mouse. Gentamycin is administered as an aqueous buffer solution (phosphate buffered saline (PBS), pH=7.4).

Coupled Bacterial Transcription/Translation Assay.

The DNA template, pBestLuc™ (Promega), is a plasmid containing a reporter gene for firefly luciferase fused to a strong tac promoter and ribosome binding site. Messenger RNA from 1 µg pBestLuc is transcribed and translated in *E. coli* S30 bacterial extract in the presence or absence of test compound. Compounds are tested in a black 96 well microtiter plate with an assay volume of 35 µL. Each test well contains: 5 µL test compound, 13 µL S30 premix (Promega), 4 µL 10× complete amino acid mix (1 mM each), 5 µL *E. coli* S30 extract and 8 µL of 0.125 µg/µL pBestLuc™. The transcription/translation reaction is incubated for 35 minutes at 37° C. followed by detection of functional luciferase with the addition of 30 µL LucLite™ (Packard). Light output is quantitated on a Packard TopCount.

Amino Acid Misincorporation Assay.

A mutant form of ubiquitin devoid of the amino acid tyrosine is produced in vitro in *E. coli* S-30 extracts in the presence of a tritiated tyrosine. Since ubiquitin has no tyrosine in the sequence, if tyrosine is used as the labeled amino acid, any incorporated counts above background are assumed to be due to the misincorporation of the tritiated amino acid. The labeled protein is captured via a ubiquitin antibody which is associated with anti-rabbit SPA beads. Altered ubiquitin molecules are not efficiently captured by the antibody. Compounds are tested in 96 well microtiter plate in an assay volume of 10 µL. Control experiments using the antibiotics, kanamycin, novabiocin, monensin, gentamicin, neomycin, tetracycline are run at 5 µM of each antibiotics.

What is claimed is:

1. A macrocyclic compound of formula (I),

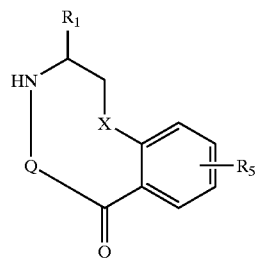

(I)

wherein:

X is O, NH or S;

Q is a bivalent linker comprising at least two amino acid residues wherein one of said amino acids is a β-amino acid;

$R_1$ is an amino acid side chain;

$R_5$ is H, OH, COOH, halogen, SH, cyano, amino, diazo, iminium, nitroso, nitro, sulfonate ester, trialkylamino, trifluoromethyl, sulfate, alkoxy, —C(O)NH$_2$, —C(O)NHR$_6$, —C(O)-(amino acid residue)$_{1-4}$, —C(O)OR$_6$, —CH$_2$OH, —CH$_2$OR$_6$, —NHC(O)R$_7$ or —NH-(amino acid residue)$_{1-4}$;

$R_6$ is alkyl optionally substituted with OH, halogen, COOH, cyano, amino, amidino, guanidino, ureido, or a nucleobase; or $R_6$ is aryl, aralkyl, a heterocycle or a heterocycle-alkyl group each optionally substituted with OH, halogen, COOH, oxo, cyano, amino, amidino, guanidino, or ureido; and $R_7$ is alkyl optionally substituted with OH, halogen, COOH, cyano, amino, amidino, guanidino, ureido or a nucleobase; or $R_7$ is aryl, aralkyl, a heterocycle or a heterocycle-alkyl group each optionally substituted with OH, halogen, C$_{1-4}$ alkyl, COOH, oxo, cyano, amino, amidino, guanidino, or ureido.

2. The compound according to claim 1 wherein X is O.

3. The compound according to claim 1 wherein Q is a dipeptide comprising a first amino acid and a second amino acid, wherein said first amino acid is β-alanine, β-aspartic acid, 2,3-diaminopropionic acid, β-homoserine or β-homotyrosine; and wherein said second amino acid is alanine, 4-aminophenylalanine, arginine, asparagine, 2,4-diaminobutyric acid, glutamic acid, glutamine, histidine, isoleucine, leucine, phenylalanine or serine.

4. The compound according to claim 1 wherein $R_1$ is the amino acid side chain of alanine, arginine, glutamic acid, glutamine, glycine, lysine, phenylalanine, serine or tyrosine.

5. The compound according to claim 1 wherein $R_5$ is NO$_2$, NH$_2$ or —NHC(O)R$_7$ in the position para to X wherein $R_7$ is NH$_2$ or alkyl substituted with NH$_2$, OH, urea, a nucleobase or a nitrogenous heterocycle optionally substituted with C$_{1-4}$ alkyl or oxo or $R_7$ is aryl substituted with urea or $R_7$ is a nitrogenous heterocycle optionally substituted with C$_{1-4}$ alkyl or oxo.

6. The compound of claim 5 wherein $R_5$ is NH$_2$ or —NHC(O)R$_7$ wherein $R_7$ is NH$_2$, pyrazin-2-yl, piperidin-4-yl, —CH$_2$-thymine, 3-urea-phenyl, urea-methyl, hydroxymethyl, 2,3-quinoxalin-7-yl, or 1-ethyl-7-methyl-1,8-napthyridin-4-one-3-yl.

7. A macrocyclic compound of formula II,

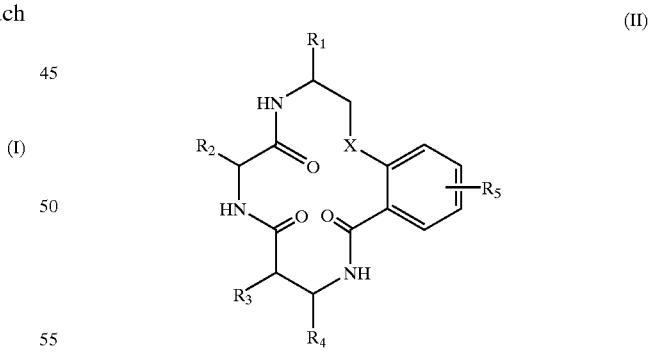

(II)

wherein:

X is O, NH or S;

$R_1, R_2, R_3$, and $R_4$ are each independently H, amino or an amino acid side chain;

$R_5$ is H, OH, COOH, halogen, SH, cyano, amino, diazo, iminium, nitroso, nitro, sulfonate ester, trialkylamino, trifluoromethyl, sulfate, alkoxy, —C(O)NH$_2$, —C(O)NHR$_6$, —C(O)-(amino acid residue)$_{1-4}$, —C(O)OR$_6$, —CH$_2$OH, —CH$_2$OR$_6$, —NHC(O)R$_7$ or —NH-(amino acid residue)$_{1-4}$;

R₆ is alkyl optionally substituted with OH, halogen, COOH, cyano, amino, amidino, guanidino, ureido, or a nucleobase; or R₆ is aryl, aralkyl, a heterocycle or a heterocycle-alkyl group each optionally substituted with OH, halogen, COOH, oxo, cyano, amino, amidino, guanidino, or ureido; and R₇ is alkyl optionally substituted with OH, halogen, COOH, cyano, amino, amidino, guanidino, ureido or a nucleobase; or R₇ is aryl, aralkyl, a heterocycle or a heterocycle-alkyl group each optionally substituted with OH, halogen, $C_{1-4}$ alkyl, COOH, oxo, cyano, amino, amidino, guanidino, or ureido.

8. The compound according to claim 7 wherein X is O.

9. The compound according to claim 7 wherein

R₁ is the amino acid side chain of alanine, arginine, glutamic acid, glutamine, glycine, lysine, phenylalanine, serine or tyrosine;

R₂ is the amino acid side chain of alanine, 4-aminophenylalanine, arginine, asparagine, 2,4-diaminobutyric acid, glutamic acid, glutamine, histidine, isoleucine, leucine, phenylalanine or serine;

R₃ is H or NH₂;

R₄ is H, NH₂ or an amino acid side chain of β-aspartic acid, β-homoserine or β-homotyrosine; and R₅ is NO₂, NH₂ or —NHC(O)R₇ in the position para to X wherein R₇ is NH₂ or alkyl substituted with NH₂, OH, urea, a nucleobase or a nitrogenous heterocycle, said nitrogenous heterocycle optionally substituted with $C_{1-4}$ alkyl or oxo, or R₇ is aryl substituted with urea, or R₇ is a nitrogenous heterocycle optionally substituted with $C_{1-4}$ alkyl or oxo.

10. The compound of claim 9 wherein R₅ is NH₂ or —NHC(O)R₇ wherein R₇ is NH₂, pyrazin-2-yl, piperidin-4-yl, —CH₂-thymine, 3-urea-phenyl, urea-methyl, hydroxymethyl, 2,3-quinoxalin-7-yl, or 1-ethyl-7-methyl-1,8-napthyridin-4-one-3-yl.

11. A compound of formula II,

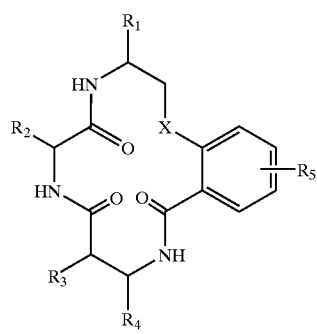

(II)

wherein:

X is O, NH or S;

R₁, R₂, R₃, and R₄ are each independently H, OH, amino, carboxyl, halogen, cycloalkyl, aryl, a heterocycle, a nucleobase or alkyl optionally substituted with OH, COOH, halogen, oxo, SH, alkylthio, amino, amido, guanidino, amidino, cycloalkyl, aryl, a heterocycle or a nucleobase wherein said cycloalkyl, aryl and heteroaryl groups are optionally substituted with OH, amino, oxo, COOH or halogen;

R₅ is H, OH, COOH, halogen, SH, cyano, amino, diazo, iminium, nitroso, nitro, sulfonate ester, trialkylamino, trifluoromethyl, sulfate, alkoxy, —C(O)NH₂, —C(O)NHR₆, —C(O)-(amino acid residue)₁₋₄, —C(O)OR₆, —CH₂OH, —CH₂OR₆, —NHC(O)R₇ or —NH-(amino acid residue)₁₋₄;

R₆ is alkyl optionally substituted with OH, halogen, COOH, cyano, amino, amidino, guanidino, ureido, or a nucleobase; or R₆ is aryl, aralkyl, a heterocycle or a heterocycle-alkyl group each optionally substituted with OH, halogen, COOH, oxo, cyano, amino, amidino, guanidino, or ureido; and R₇ is alkyl optionally substituted with OH, halogen, COOH, cyano, amino, amidino, guanidino, ureido or a nucleobase; or R₇ is aryl, aralkyl, a heterocycle or a heterocycle-alkyl group each optionally substituted with OH, halogen, $C_{1-4}$ alkyl, COOH, oxo, cyano, amino, amidino, guanidino, or ureido.

12. The compound according to claim 11 wherein

X is O;

R₁ and R₂ are independently H, NH₂, COOH or alkyl optionally substituted with OH, SH, alkylthio, NH₂, COOH, amido, guanidino, aryl, OH-substituted aryl, a nitrogenous heterocycle;

R₃ is H, NH₂;

R₄ is H, COOH, hydroxyalkyl or 4-hydroxyphenyl; and

R₅ is NO₂, NH₂ or —NHC(O)R₇ in the position para to X wherein R₇ is NH₂ or alkyl substituted with NH₂, OH, urea, a nucleobase or a nitrogenous heterocycle optionally substituted with $C_{1-4}$ alkyl or oxo or R₇ is aryl substituted with ureido or R₇ is a nitrogenous heterocycle optionally substituted with $C_{1-4}$ alkyl or oxo.

13. The compound according to claim 12 wherein R₅ is NH₂ or —NHC(O)R₇ wherein R₇ is NH₂, pyrazin-2-yl, piperidin-4-yl, —CH₂-thymine, 3-urea-phenyl, urea-methyl, hydroxymethyl, 2,3-quinoxalin-7-yl, or 1-ethyl-7-methyl-1,8-napthyridin-4-one-3-yl.

14. A compound having the formula:

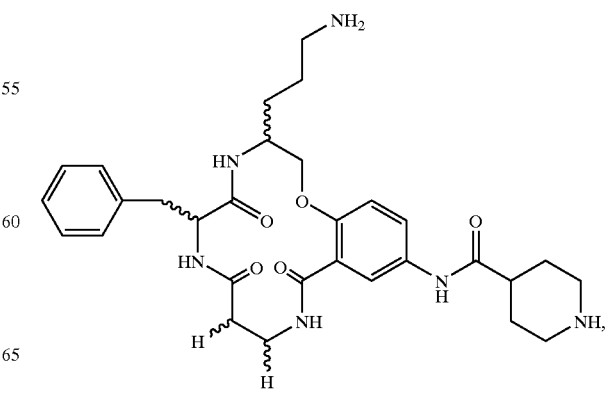

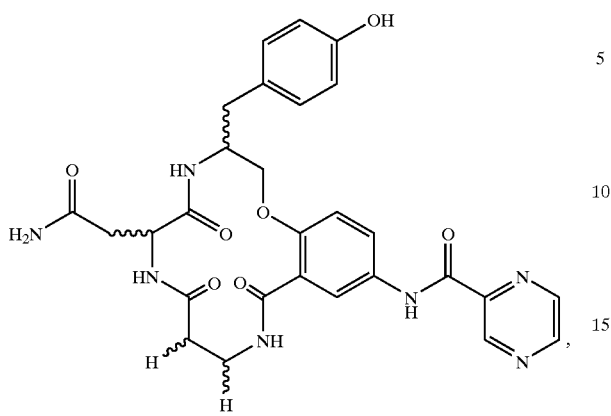

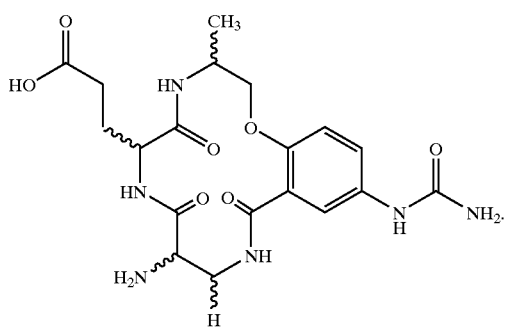

15. A macrocyclic compound of the formula (I),

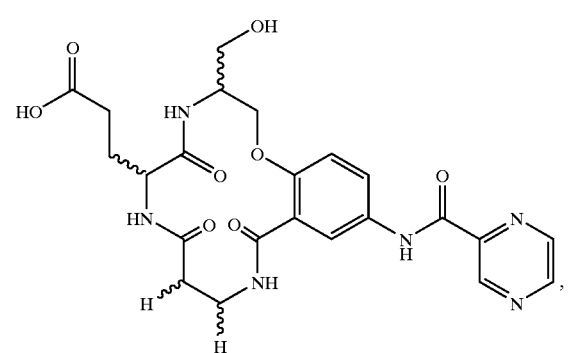

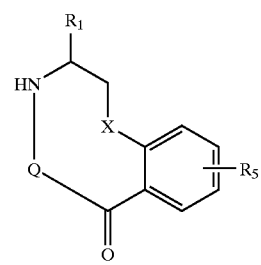

(I)

wherein:
X is O, NH or S;
Q is a bivalent linker comprising at least two amino acid residuals wherein one of said amino acids is a β-amino acid;
$R_1$ is an amino acid side chain; and
$R_5$ is an electron withdrawing group.

16. A macrocyclic compound of formula II,

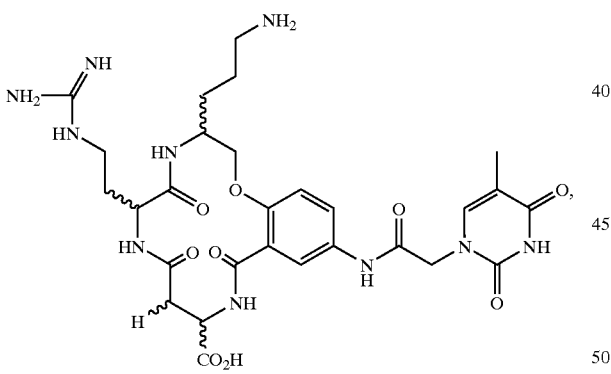

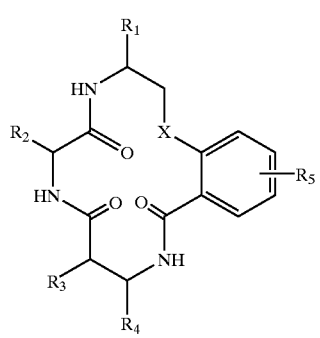

(II)

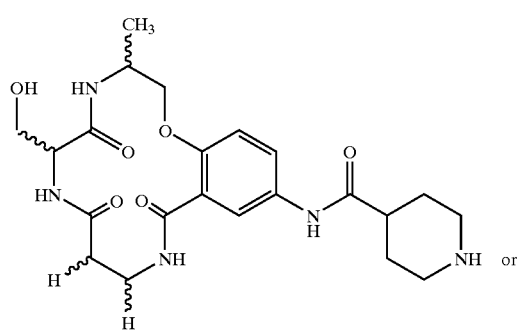

wherein:
X is O, NH or S;
$R_1$, $R_2$, $R_3$, and $R_4$ are each independently H, amino or an amino acid side chain; and
$R_5$ is an electron withdrawing group.

17. A compound of formula II,

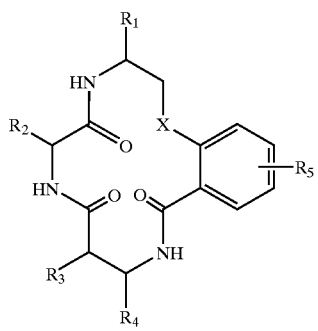

(II)

wherein:

X is O, NH or S;

$R_1$, $R_2$, $R_3$, and $R_4$ are each independently H, OH, amino, carboxyl, halogen, cycloalkyl, aryl, a heterocycle, a nucleobase or alkyl optionally substituted with OH, COOH, halogen, oxo, SH, alkylthio, amino, amido, guanidino, amidino, cycloalkyl, aryl, a heterocycle or a nucleobase wherein said cycloalkyl, aryl and heteroaryl groups are optionally substituted with OH, amino, oxo, COOH or halogen; and $R_5$ is an electron withdrawing group.

18. A process for preparing macrocyclic compounds or solid support-bound compound of formula (IIa),

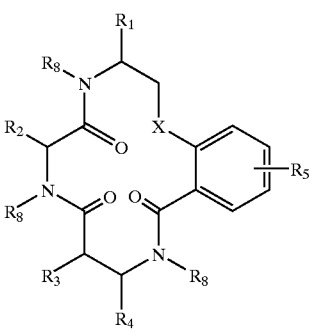

(IIa)

wherein:

X is O, NH or S;

$R_1$, $R_2$, $R_3$, and $R_4$ are each independently H, amino or an amino acid side chain;

$R_5$ is H, OH, COOH, halogen, SH, cyano, amino, diazo, iminium, nitroso, nitro, sulfonate ester, trialkylamino, trifluoromethyl, sulfate, alkoxy, —C(O)NH$_2$, —C(O)NHR$_6$, —C(O)-(amino acid residue)$_{1-4}$, —C(O)OR$_6$, —CH$_2$OH, —CH$_2$OR$_6$, —NHC(O)R$_7$ or —NH-(amino acid residue)$_{1-4}$;

$R_6$ is alkyl optionally substituted with OH, halogen, COOH, cyano, amino, amidino, guanidino, ureido, or a nucleobase; or $R_6$ is aryl, aralkyl a heterocycle or a heterocycle-alkyl group each optionally substituted with OH, halogen, COOH, oxo, cyano, amino, amidino, guanidino, or ureido;

$R_7$ is alkyl optionally substituted with OH, halogen, COOH, cyano, amino, amidino, guanidino, ureido or a nucleobase; or $R_7$ is aryl, aralkyl, a heterocycle or a heterocycle-alkyl group each optionally substituted with OH, halogen, $C_{1-4}$ alkyl, COOH, oxo, cyano, amino, amidino, guanidino, or ureido; and $R_8$ is H or a solid support, provided that no more than one $R_8$ is a solid support; comprising cyclizing a compound or solid support-bound compound of formula (III)

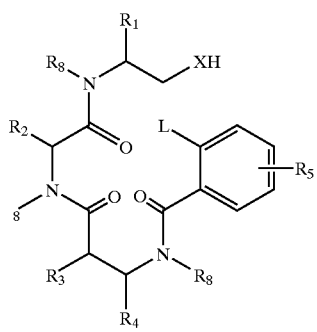

(III)

wherein L is a leaving group;

for a time and under conditions effective to achieve aromatic nucleophilic substitution.

19. The process according to claim 18, wherein one $R_8$ is a solid support, the process further comprising the step of cleaving the macrocyclic compound from said solid support.

20. The process according to claim 18, wherein $R_5$ is an electron withdrawing group para to L.

21. The process according to claim 18, wherein said compound of formula (III) is prepared by a) reacting a solid support-bound compound of formula (IV)

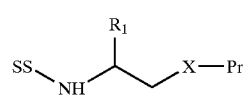

(IV)

wherein SS is a solid support and Pr is a protecting group;

with an α-amino acid having a protected α-amino group and a side chain $R_2$ for a time and under conditions to produce a compound of formula (V)

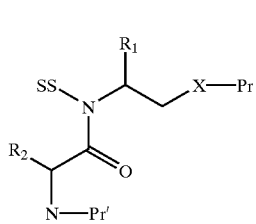

(V)

wherein Pr' is an amino protecting group;

b) removing the protecting group from the α-amino group to produce a first solid support-bound compound;

c) reacting the first solid support-bound compound with a β-amino acid having a protected β-amino group and α and β side chains defined by $R_3$ and $R_4$ respectively for a time and under conditions effective to produce a compound of formula (VI)

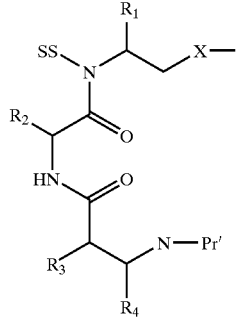

(VI)

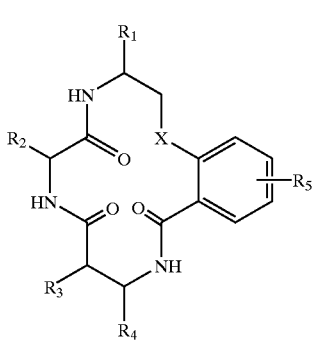

(III)

d) removing the amino protecting group from the β-amino group to produce a second solid support-bound compound;

e) reacting the second solid support-bound compound with a compound of formula (VII)

(VII)

for a time and under conditions effective to produce said compound of formula (III).

22. The process according to claim 21, wherein $R_5$ is an electron withdrawing group para to L.

23. A process for preparing macrocyclic compounds or solid support-bound compound of formula (IIa),

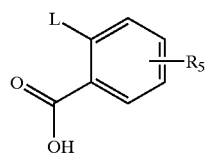

(IIa)

wherein:

X is O, NH or S;

$R_1$, $R_2$, $R_3$, and $R_4$ are each independently H, amino or an amino acid side chain;

$R_5$ is an electron withdrawing group; and $R_8$ is H or a solid support, provided that no more than one $R_8$ is a solid support;
comprising cyclizing a compound or solid support-bound compound of formula (III)

wherein L is a leaving group, for a time and under conditions to achieve aromatic nucleophilic substitution.

24. A process for preparing macrocyclic compounds of formula II

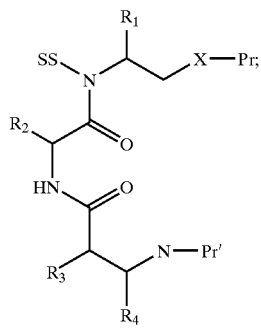

(II)

wherein:

X is O, NH or S;

$R_1$, $R_2$, $R_3$, and $R_4$ are each independently H, amino or an amino acid side chain;

$R_5$ is H, OH, COOH, halogen, SH, cyano, amino, diazo, iminium, nitroso, nitro, sulfonate ester, trialkylamino, trifluoromethyl, sulfare, alkoxy, —C(O)NH$_2$, —C(O)NHR$_6$, —C(O)-(amino acid residue)$_{1-4}$, —C(O)OR$_6$, —CH$_2$OH, —CH$_2$OR$_6$, 13 NHC(O)R$_7$ or —NH-(amino acid residue)$_{1-4}$;

$R_6$ is alkyl optionally substituted with OH, halogen, COOH, cyano, amino, amidino, guanidino, ureido, or a nucleobase; or $R_6$ is aryl, aralkyl a heterocycle or a heterocycle-akyl group each optionally substituted with OH, halogen, COOH, oxo, cyano, amino, amidino, guanidino, or ureido; and $R_7$ is alkyl optionally substituted with OH, halogen, COOH, cyano, amino, amidino, guanidino, ureido or a nucleobase; or $R_7$ is aryl, aralkyl, a heterocycle or a heterocycle-akyl group each optionally substituted with OH, halogen, C$_{1-4}$ alkyl, COOH, oxo, cyano amino, amidino, guanidino, or ureido; said process comprising, cyclizing a compound or solid support-bound compound of formula (III)

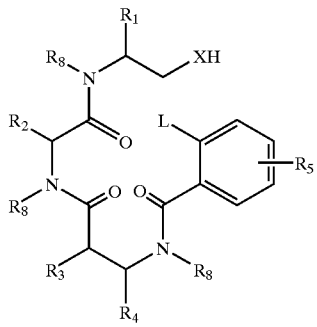

(III)

wherein:
L is a leaving group; and
$R_8$ is H or a solid support, provided that no more than one $R_8$ is a solid support;
for a time and under conditions effective to achieve aromatic nucleophilic substitution.

25. The process according to claim 24, wherein one $R_8$ is a solid support, the process further comprising the step of cleaving from said solid support the macrocyclic compound of formula II.

26. A process for preparing macrocyclic compounds of formula II,

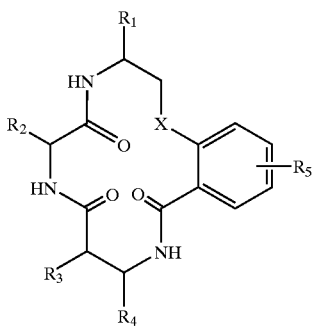

(II)

wherein;
X is O, NH or S;
$R_1$, $R_2$, $R_3$, and $R_4$ are each independently H, amino or an amino acid side chain; and
$R_5$ is an electron withdrawing group; said process comprising, cyclizing a compound or solid support-bound compound of formula (III)

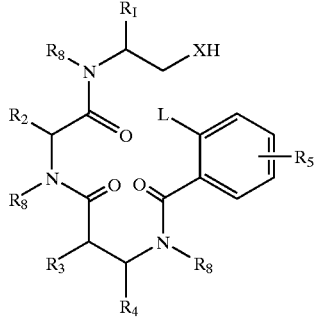

(III)

wherein:
L is a leaving group; and
$R_8$ is H or a solid support, provided that no more than one $R_8$ is a solid support;
for a time and under conditions to achieve aromatic nucleophilic substitution.

27. The process according to claim 26, wherein one $R_8$ is a solid support, the process further comprising the step of cleaving from said solid support the macrocyclic compound of formula II.

28. A method of inhibiting growth of bacteria comprising administering to a mammal in need thereof a compound of claim 1 for a time and under conditions effective to inhibit growth of said bacteria.

29. The method according to claim 28, wherein said mammal is a human.

30. The method according to claim 28, wherein said bacteria is Staphylococcus, Lactobacillus, Streptococcus, Sarcina, Escherichia, Enterobacter, Klebsiella, Pseudomonas, Acinetobacter, Proteus, Campylobacter, Citrobacter, Nisseria, Baccillus, Bacteroides, Peptococcus, Clostridium, Salmonella, Shigella, Serratia, Haemophilus or Brucella.

31. The method according to claim 28, wherein said bacteria is *Streptococcus pyogenes, Enterococcus faecalis, Escherichia coli, Klebsiella pneumoniae* or *Staphylococcus aureus.*

* * * * *

UNITED STATES PATENT AND TRADEMARK OFFICE
CERTIFICATE OF CORRECTION

PATENT NO. : 6,660,832 B1
DATED : December 19, 2003
INVENTOR(S) : Elizabeth Jefferson et al.

It is certified that error appears in the above-identified patent and that said Letters Patent is hereby corrected as shown below:

Title page,
Item [56], References Cited, OTHER PUBLICATIONS,
"Marsh" reference, please delete "6199-6202" and insert therefor -- 6199-6203 --;
"Bilodeau" reference, please delete "Stragegy" and insert therefor -- Strategy --;

Column 40,
Line 38, please delete "residuals" and insert therefor -- residues --;
Line 64, please delete "arc" and insert therefor -- are --;

Column 44,
Line 48, please delete "sulfare" and insert therefor -- sulfate --;
Line 50, please delete "13" and insert therefor -- - --;
Lines 55 and 61, please delete "heterocycle-akyl" and insert therefor -- heterocycle-alkyl --;

Signed and Sealed this

Twenty-second Day of March, 2005

JON W. DUDAS
*Director of the United States Patent and Trademark Office*